United States Patent [19]

Cho et al.

[11] Patent Number: 5,242,890

[45] Date of Patent: Sep. 7, 1993

[54] 1,2,4-OXADIAZOLE DERIVATIVE, USEFUL AS SELECTIVE HERBICIDE

[75] Inventors: Kwang Y. Cho; In H. Jeong; Young S. Kim; Beom T. Kim; Yong K. Min; Geun S. Jeon; Jin S. Kim; Kyung S. Hong; In T. Hwang; Suk J. Koo, all of Daejeon, Rep. of Korea

[73] Assignee: Korea Research Institute of Chemical Technology, Rep. of Korea

[21] Appl. No.: 829,976

[22] Filed: Feb. 3, 1992

Related U.S. Application Data

[63] Continuation of Ser. No. 373,807, Jun. 29, 1989, abandoned.

[30] Foreign Application Priority Data

Jul. 7, 1988 [KR] Rep. of Korea ............ 8435/1988[U]

[51] Int. Cl.$^5$ .................. C07D 271/06; A01N 43/82
[52] U.S. Cl. .................... 504/100; 548/119; 548/131; 548/132; 548/133
[58] Field of Search ............... 548/131, 132, 133, 119; 71/92

[56] References Cited

U.S. PATENT DOCUMENTS 4,753,671 6/1988 Someya .................................. 71/92

FOREIGN PATENT DOCUMENTS 3408528 9/1985 Fed. Rep. of Germany .......... 71/92

Primary Examiner—Robert Gerstl
Attorney, Agent, or Firm—Gifford, Groh, Sprinkle, Patmore and Anderson

[57] ABSTRACT

The present invention relates to 1,2,4-oxadiazole derivative of the formula (I)

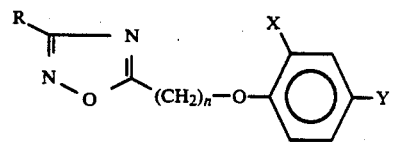

wherein
X represents a chlorine or fluorine atom or methyl group,
Y represents a chlorine or fluorine atom,
n is an integer of 1 or 3.

The compounds of the invention have a extremely high selectively between paddy rice or crop plants and weeds, and a strong activity on various weeds. Moreover, the compounds have a very low phytotoxicity to paddy rice and crop plants.

4 Claims, No Drawings

1,2,4-OXADIAZOLE DERIVATIVE, USEFUL AS SELECTIVE HERBICIDE

This application is a continuation of Ser. No. 07/373,807, filed Jun. 29, 1989, now abandoned.

BACKGROUND OF THE INVENTION

1. Field of the Invention

The present invention relates to novel 1,2,4-oxadiazole derivatives having an excellent herbicidal activity, methods of preparation therefore and the herbicidal composition comprising it.

2. Description of the Invention

Phenoxy type herbicides such as 2,4-D, 2,4,5-T, MCPA and MCPB have been employed as post-emergence application to control paddy and upland weeds. Since the phenoxy type herbicides cause the severe phytotoxicity to paddy rice and crop pants depending on the timing of application or the weather conditions, it has been strongly desired to develop a new type of herbicide which is able to overcome the phytotoxicity on paddy rice and crop plants and control annual and perennial weeds in paddy and upland field. In other words, a new type of herbicide should have an extremely high selectivity between paddy rice or crop plants and weeds and a strong activity on weeds.

SUMMARY OF THE INVENTION

Under the above circumstances, the present inventors conducted intensive studies for developing herbicides having low phytotoxicity to paddy rice and crop plants and high selectively between paddy rice or crop plants and weeds. They found that 1,2,4-oxadiazole derivative of the following formula(I) has low phytotoxicity, high selectivity and strong activity.

Accordingly, it is an object of the invention to provide a new type of herbicide which can industrially be produced and which is able to control annual and perennial weed in paddy and upland field with keeping high selectivity between crops and weeds.

DETAILED DESCRIPTION OF THE INVENTION

The present invention relates to 1,2,4-oxadiazole derivative of the formula(I)

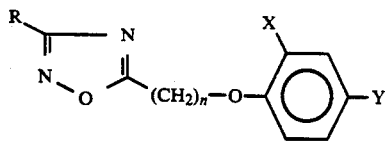

wherein
X represents a chlorine or fluorine atom or methyl group,
Y represents a chlorine or fluorine atom,
n is an integer of 1 or 3, and
R represents a $C_{3-7}$ alkyl group; a benzyl group substituted by bromine atom, chlorine atom, fluorine atom, $C_{1-2}$ alkyl, nitro, amino, acetylamino, thioethoxycarbonylamino, diethylcarbamyl or dimethoxy group; a phenoxymethyl group substituted by chlorine atom or fluorine atom; a methyl group substituted by bromine atom, chlorine atom, fluorine atom, hydroxy, acetate, haloacetate, $C_{1-2}$ alkylcarbamate, phenoxybenzoate, methylsulfonate, phenoxyacetate, ethyloxalate, $C_{1-3}$ alkylamino, fluorophenylamino, phthalimide, phenylsulfonylamino, pyrrolidine, thiophenoxy, ethyldithiophosphonate, phenylsulfonyl, diethylthiocarbamate, aminocarbamyl or ethoxycarbonyl group; a phenyl group substituted by chlorine atom, fluorine atom, methoxy or fluoromethyl group; a $C_{2-3}$ alkoxy or phenoxy group unsubstituted or substituted by chlorine atom, fluorine atom or $C_2$ alkoxy group; an amino group unsubstituted or substituted by $C_5$ alkyl, acetyl, $C_{1-2}$ alkoxycarbonyl, methylcarbamyl, phenylsulfonyl; a bromine or chlorine atom; a carbonyl group substituted by $C_{1-4}$ alkylamino, $C_{1-2}$ alkoxy, amino, azido, halophenylamino, acetylamino, methylsulfonylamino, $C_{1-4}$ alkyl, benzyl or phenyl group; an oxime group substituted by $C_{1-4}$ alkyl or phenyl group; or an imine group substituted by $C_{1-2}$ alkoxy, amino, hydroxyamino, ethylphosphonyl or chlorine atom.

The compounds of formula(I) of this invention can be prepared, for example, by the following processes:

(1) Method 1

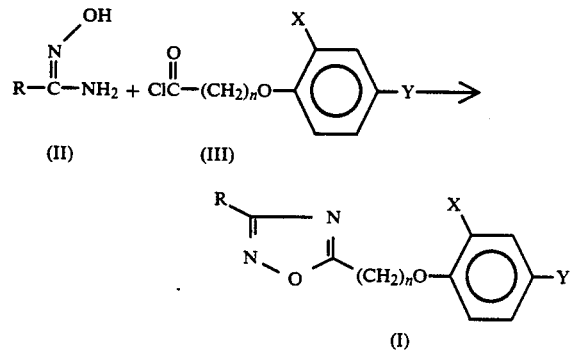

wherein
X represents chlorine atom or methyl group,
Y represents chlorine atom,
n is an integer of 1 or 3, and
R represents $C_{3-7}$ alkyl group; a substituted benzyl group; a halomethyl group; a substituted phenoxymethyl group; a substituted phenyl group; a $C_{2-3}$ alkoxy or substituted phenoxy group; an ester group; or an ester methyl group.

In other words, the compound(I) of this invention can be prepared by reacting the compound(II) with acylchloride of the compound(III).

The above reaction is carried out at reflux temperature in the presence of a catalyst for 1 to 5 hours. Various solvents can be used in this invention, which include acetone, alcohol, dioxane, etc. For the catalyst, dimethylamine, trimethylamine, boron trifluoride etherate, sodium methoxide, etc. may be used.

(2) Method 2

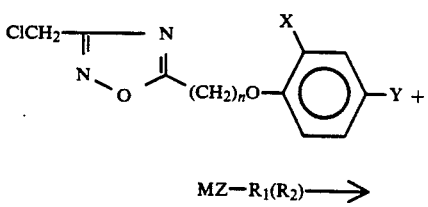

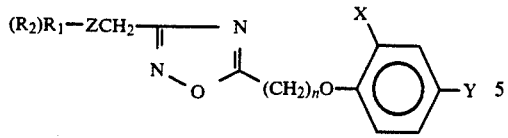

wherein,
X represents chlorine atom or methyl group,
Y represents chlorine atom,
n is an integer of 1 or 3,
M represents hydrogen or sodium atom,
Z is nitrogen, oxygen or sulfur atom, and
if Z is a nitrogen atom, $R_1$ or $R_2$ is a $C_{1-2}$ alkyl group, hydrogen atom, a substituted phenyl group, an aryl sulfonyl group or a cyclized acyl group; and
if Z is oxygen or sulfur atom, $R_1$ is a phenyl group or a substituted carbonyl group.

The above reaction is carried out at reflux temperature in the presence of base. Various solvents can be used in this reaction, which include acetone, dioxane, toluene or xylene, tetrahydrofuran, acetonitrile, etc. For the base, they may be employed pyridine, triethylamine, potassium carbonate, sodium hydride, etc.

(3) Method 3

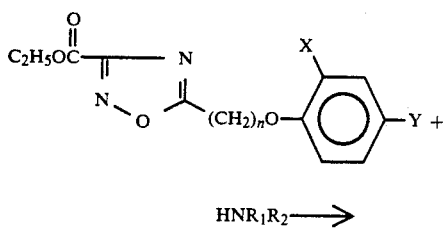

wherein
X represents chlorine atom or methyl group,
Y represents chlorine atom,
n is an integer of 1 or 3, and
each of $R_1$ and $R_2$, which may be same or different, represents a hydrogen atom, $C_{1-4}$ alkyl group, an acyl group, a sulfonyl group, an unsubstituted or substituted phenyl group, an amino group or a methoxy group.

The above reaction is carried out at room temperature in the organic solvent for 30 minutes to 1 hour. For the solvent, alcohol such as methanol, ethanol and isopropanol, acetone, acetonitrile, tetrahydrofuran, etc. can be used.

(4) Method 4

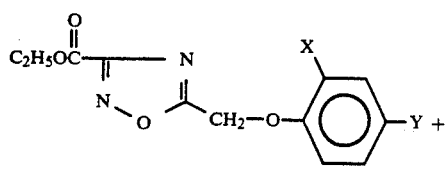

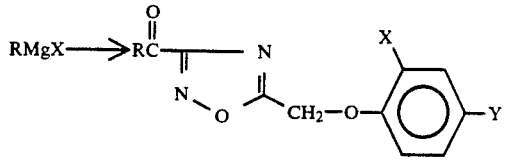

wherein
X and Y represent chlorine atoms,
R represents $C_{1-4}$ alkyl group, a benzyl group or phenyl group.

The above reaction is proceeded for 1 to 2 hours at $-78°$ C. in the organic solvent. For the solvent, tetrahydrofuran, diethyl ether can be used.

(5) Method 5

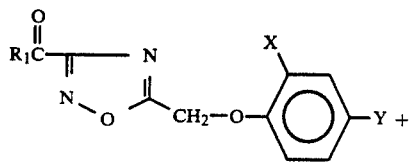

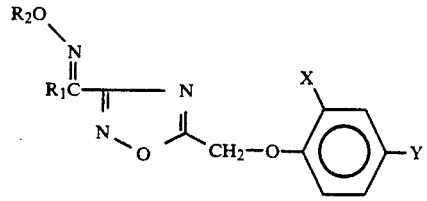

wherein
X and Y represent chlorine atoms,
R represents $C_{1-4}$ alkyl group or a phenyl group and
$R_2$ represents a hydrogen atom or $C_{2-3}$ alkyl group.

The above reaction is carried out at reflux temperature in the presence of the organic solvent. For the solvent, alcohol such as methanol, ethanol and isopropanol, acetone, acetonitrile, tetrahydrofuran, etc. can be used.

(6) Method 6

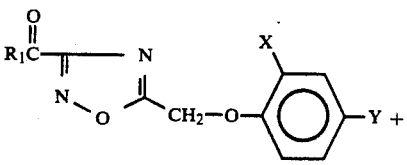

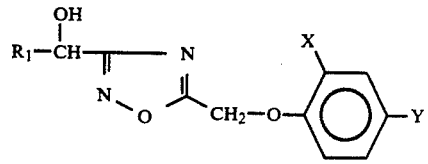

wherein,
X and Y represent chlorine atoms and
$R_1$ represents $C_{1-3}$ alkyl group unsubstituted or substituted by methoxy group.

The above reaction is carried out at reflux temperature in the presence of the organic solvent. For the solvent, isopropyl alcohol can be used.

(7) Method 7

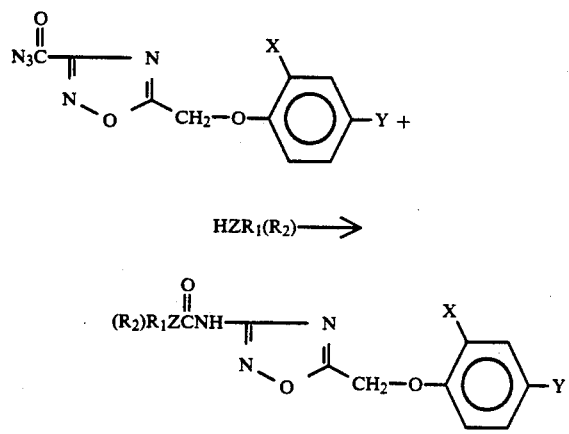

HZR₁(R₂) ⟶ wherein,

X and Y are chlorine atoms,

Z is a nitrogen or oxygen atom, and if Z is a nitrogen atom, $R_1$ or $R_2$ is a hydrogen atom or $C_{1-2}$ alkyl group; and if Z is an oxygen atom, $R_1$ is $C_{1-3}$ alkyl group.

The above reaction process is carried out a reflux temperature in the presence of the organic solvent for 1 hour and subsequently at room temperature for 15 hours. For the solvent, alcohol such as methanol, ethanol and propanol can be used in order to prepare carbamate group. However, the reaction should be furthermore carried out for 1 to 4 hours at reflux temperature in the presence of dioxane as a solvent to prepare urea group.

(8) Method 8

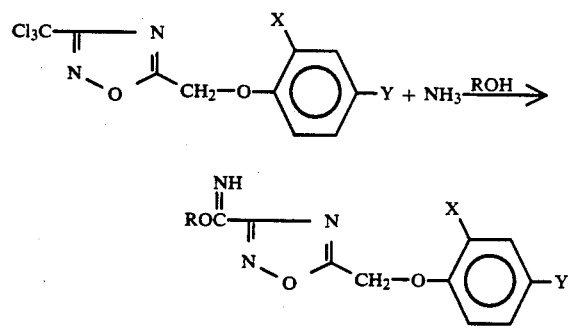

wherein

X and Y are chlorine atoms, and

R represents $C_{1-2}$ alkyl group.

The above reaction process is carried out at room temperature in the presence of the organic solvent for 3 to 4 hours. For the solvent, alcohol such as methanol or ethanol can be used.

(9) Method 9

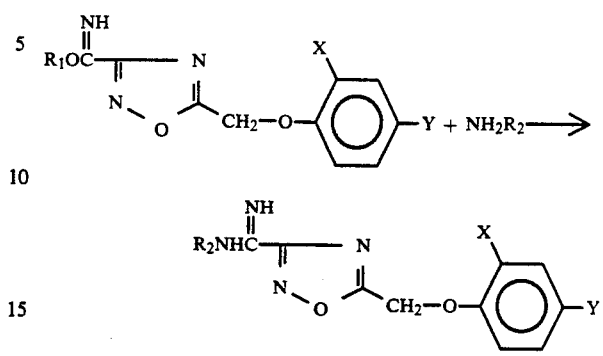

wherein

X and Y represent chlorine atoms, $R_1$ represents $C_{1-2}$ alkyl group, and $R_2$ represents a hydrogen atom or hydroxy group.

The above reaction is carried out at room temperature in the presence of the organic solvent for 24 hours. For the solvent, alcohol such as methanol or ethanol can be used.

After the reaction is completed, the final product can be separated and/or purified by the conventional methods, if necessary. For instance, the reaction mixture is washed with water, followed by distillation of the solvent, and the residue being purified by column chromatography to obtain the compound(I) with a high yield.

Other features of the invention will become apparent in the course of the following description of the exemplary embodiments which are given for illustration of the invention and are not intended to be limiting thereof.

EXAMPLES

Example 1

3-n-propyl-5[(2,4-dichlorophenoxy)methyl]-1,2,4-oxadiazole. Compound No. 1

1.02 g of butylamidoxime, 2.40 g of 2,4-dichlorophenoxyacetyl chloride and 0.14 g of borontrifluoride etherate were added to 50 ml of toluene. The mixture was heated to reflux for 6 hours. After completion of reaction, the mixture was washed with 100 ml water and then subjected to distillation of toluene, and the residue was purified by column chromatography using a mixture of solvent(benzene:ether=4:1) to obtain 1 g of the desired compound(yield: 69.7%).

Example 2

3-allyl-5-[(2-chloro-4-fluorophenoxy)methyl]-1,2,4-oxadiazole: Compound No. 145

0.71 g of 2-chloro-4-fluorophenol, 0.77 g of 3-allyl-5-chloromethyl-1,2,4-oxadiazole and 0.83 of potassium carbonate were added to 20 ml of acetone. After completion of the reaction, the resulting precipitates were filtered out from the mixture and then acetone was removed by distillation, and the residue was purified by column chromatography (benzene:hexane=1:1) to obtain 1.05 g of the desired product(yield: 80.8%).

Example 3

3-diethylcarbamyl-5-[(2,4-dichlorophenoxy)methyl]-1,2,4-oxadizaole: Compound No. 99

1.58 g of 3-ethoxycarbonyl-5-[(2,4-dichlorophenoxy)methyl]-1,2,4-oxadiazole and 0.73 g of diethylamine were added to 30 ml of methanol. The mixture was stirred at room temperature for 1 hour. The resulting precipitates were filtered out from the reaction mixture and then washed with 50 ml of methanol. Upon drying the white solid, 1.46 g of the desired product (yield: 84.9%) was obtained.

Example 4

3-ethylcarbonyl-5-[(2,4-dichlorophenoxy)methyl]-1,2,4-oxadiazole: Compound No. 112

0.95 g of 3-ethoxycarbonyl-5-[(2,4-dichlorophenoxy)methyl]-1,2,4-oxadiazole was added to 30 ml of tetrahydrofuran. The mixture was cooled to −78° C., and then 3 ml of ethylmagnesium bromide (2M solution) was added dropwise. After the mixture was stirred at −78° C. for 1 hour, it was poured into cold aqueous 5% HCl solution. After the resulted product was extracted with ether and concentrated, it was purified by column chromatography(hexane:ethylacetate=4:1) to obtain 0.75 g of the desired product(yield: 83.0%).

Example 5

3-(alpha-hydroxyiminopropyl)-5-[(2,4-dichlorophenoxy)methyl]-1,2,4-oxadiazole: Compound No. 119

0.9 g of 3-ethylcarbonyl-5-[(2,4-dichlorophenoxy)methyl]-1,2,4-oxadiazole and 0.21 g of hydroxyamine hydrochloride were added to 10 ml of methanol. The mixture was heated to reflux for 4 hours. After evaporation of methanol, water was added to the residue. The aqueous solution was extracted with ethylacetate. After evaporation of ethylacetate, the residue was purified by column chromatography(benzene:ether=1.1) to provide 0.80 g of the desired product(yield: 85.0%).

Example 6

3-(1-hydroxybutyl)-5-[(2,4-dichlorophenoxy)methyl]-1,2,4-oxadiazole: Compound No. 138

0.316 g of 3-propylcarbonyl-5-[(2,4-dichlorophenoxy)methyl]-1,2,4-oxadiazole and 0.20 g of aluminum isopropoxide were added to 10 ml of isopropanol. The mixture was heated to reflux for 48 hours. After evaporation of isopropanol, water was added to the residue. The aqueous solution was extracted with ethylacetate. After evaporation of ethylacetate, the residue was purified by column chromatography(hexane:ethylacetate=3:2) to provide 0.17 g of the desired product(yield: 54.0%).

Example 7

3-N,N-dimethylureido-5-[(2,4-dichlorophenoxy)methyl]-1,2,4-oxadiazole: Compound No. 80

1.57 g of 3-azidocarbonyl-5-[(2,4-dichlorophenoxy)methyl]-1,2,4-oxadiazole was added to 20 ml of dioxane. After the mixture was refluxed for 1 hour, 0.30 g of dimethylamine was added with formation of bubble and then the mixture was stirred at room temperature for 15 hours. The resulting precipitates were filtered from the mixture and washed with dioxane. Upon drying the precipitates, 0.9 g of the desired product was obtained (yield: 55.0%).

Example 8

3-(iminomethoxymethyl)-5-[(2,4-dichlorophenoxy)methyl]-1,2,4-oxadiazole: Compound No. 125

2.17 g of 3-(trichloromethyl)-5-[(2,4-dichlorophenoxy)methyl]-1,2,4-oxadiazole was added to 50 ml of methanol. An excess of ammonia gas was added with formation of bubble at 0° C. and then the mixture was stirred at room temperature for 4 hours. After evaporation of methanol, water was added to the residue. The aqueous solution was extracted with ethylacetate. After evaporation of ethylacetate, the residue was purified by column chromatography(hexane:ethylacetate) to provide 0.92 g of the desired product(yield: 50.9%).

Example 19

3-iminoaminomethyl-5-[(2,4-dichlorophenoxy)methyl]-1,2,4-oxadiazole: Compound No. 128

0.62 g of 3-iminomethoxymethyl-5-[(2,4-dichlorophenoxy)methyl]-1,2,4-oxadiazole was added to 20 ml of methanol. An excess of ammonia gas was added with formation of bubble at 0° C. and then the mixture was stirred at room temperature for 24 hours. The resulting white precipitates were filtered from the reaction mixture and then washed with methanol. Upon drying the white precipitates, 0.54 g of the desired product was obtained(yield: 94.4%).

The typical compounds prepared by the similar method to the above examples are shown in Table 1 together with their physical properties.

TABLE 1

[Structure: R-C(=N-O-(CH₂)ₙ-O-phenyl(X,Y))]

| Compound No. | R | n | X | Y | Physical properties | Element analysis (%) Calculated value (Measured value) C | H | N | NMR (δ, ppm) |
|---|---|---|---|---|---|---|---|---|---|
| 1 | CH₃CH₂CH₂— | 1 | Cl | Cl | mp 39–40° C. | 50.19 (50.33) | 4.21 (4.28) | 9.75 (9.57) | 7.25–6.80(m, 3H), 5.15(s, 2H), 2.72(s, 2H), 1.92–1.52(m, 2H), 0.98(t, 3H) |
| 2 | (CH₃)₂CH— | 1 | Cl | Cl | oil | 50.19 (50.08) | 4.21 (4.18) | 9.75 (9.83) | 7.20–6.80(m, 3H), 5.20(s, 2H), 3.24–2.87(m, 1H), 1.30(d, 6H) |
| 3 | (CH₃)₃C— | 1 | Cl | Cl | mp 33–34° C. | 51.85 (51.90) | 4.69 (4.65) | 9.30 (9.22) | 7.30–6.80(m, 3H), 5.25(s, 2H), 1.35(s, 9H) |
| 4 | CH₂=CHCH₂— | 1 | Cl | Cl | oil | 50.55 (50.58) | 3.54 (3.49) | 9.82 (9.78) | 7.40–6.80(m, 3H), 6.30–5.70(m, 1H), 5.35–5.10(m, 4H), 3.65–3.45(m, 2H) |
| 5 | cyclohexenyl-CH₂— | 1 | Cl | Cl | mp 40–41° C. | 56.65 (56.60) | 4.76 (4.83) | 8.26 (8.28) | 7.25–6.85(m, 3H), 5.40(m, 1H), 5.20(s, 2H), 3.25(s, 2H), 2.10–1.85(m, 4H), 1.75–1.42(m, 4H) |
| 6 | 4-F-C₆H₄-CH₂— | 1 | Cl | Cl | oil | 54.41 (54.25) | 3.12 (3.18) | 7.93 (7.80) | 7.27–6.65(m, 7H), 5.10(s, 2H), 3.90(s, 2H) |
| 7 | 4-Br-C₆H₄-CH₂— | 1 | Cl | Cl | mp 65–66° C. | 46.41 (46.47) | 2.68 (2.70) | 6.76 (6.67) | 7.30–6.65(m, 7H), 5.02(s, 2H), 3.80(s, 2H) |
| 8 | 2-Cl-6-F-C₆H₃-CH₂— | 1 | Cl | Cl | mp 75–76° C. | 49.58 (49.62) | 2.60 (2.65) | 7.23 (7.17) | 7.30–6.70(m, 6H), 5.30(s, 2H), 4.20(s, 2H) |

TABLE 1-continued

Structure: R-C(=N-O-(CH₂)n-O-Ar(X)(Y))

| Compound No. | R | n | X | Y | Physical properties | Element analysis (%) Calculated value (Measured value) C | H | N | NMR (δ, ppm) |
|---|---|---|---|---|---|---|---|---|---|
| 9 | 3-CH₃-C₆H₄-CH₂- | 1 | Cl | Cl | mp 42–43° C. | 58.47 (58.42) | 4.04 (4.09) | 8.02 (8.11) | 7.10–6.80(m, 7H), 5.00(s, 2H), 4.10(s, 2H), 2.20(s, 3H) |
| 10 | 4-CH₃CH₂-C₆H₄-CH₂- | 1 | Cl | Cl | mp 33–34° C. | 59.52 (59.60) | 4.44 (4.51) | 7.71 (7.59) | 7.30–6.70(m, 7H), 5.10(s, 2H), 3.95(s, 2H), 2.50(q, 2H), 1.18(t, 3H) |
| 11 | 3-CF₃-C₆H₄-CH₂- | 1 | Cl | Cl | oil | 50.64 (50.73) | 2.75 (2.71) | 6.95 (6.92) | 7.50–6.70(m, 7H), 5.15(s, 2H), 4.10(s, 2H) |
| 12 | 3,4-methylenedioxy-C₆H₃-CH₂- | 1 | Cl | Cl | mp 87–88° C. | 53.85 (53.78) | 3.19 (3.22) | 7.39 (7.43) | 7.30–6.70(m, 6H), 5.80(s, 2H), 5.25(s, 2H), 3.90(s, 2H) |
| 13 | 4-O₂N-C₆H₄-CH₂- | 1 | Cl | Cl | mp 68–69° C. | 50.55 (50.50) | 2.92 (2.91) | 11.05 (11.08) | 8.00–6.80(m, 7H), 5.20(s, 2H), 4.05(s, 2H) |
| 14 | 4-H₂N-C₆H₄-CH₂- | 1 | Cl | Cl | mp 95–95° C. | 54.88 (54.82) | 3.74 (3.69) | 12.00 (12.09) | 7.20–6.40(m, 7H), 5.20(s, 2H), 4.00(bs, 2H), 3.88(s, 2H) |

TABLE 1-continued

![structure: R-C(=N-O-(CH2)n-O-phenyl(X,Y))]

| Compound No. | R | n | X | Y | Physical properties | Element analysis (%) Calculated value (Measured value) C | H | N | NMR (δ, ppm) |
|---|---|---|---|---|---|---|---|---|---|
| 15 | 4-(CH₃NHC(=O))-C₆H₄-CH₂- | 1 | Cl | Cl | mp 87-88° C. | 55.12 (55.16) | 3.85 (3.88) | 10.71 (10.68) | 7.50-6.95(m, 7H), 5.15(s, 2H), 4.20(s, 2H), 3.10(bs, 1H), 1.95(s, 3H) |
| 16 | 4-(CH₃CH₂SC(=O)NH)-C₆H₄-CH₂- | 1 | Cl | Cl | mp 80-81° C. | 52.06 (51.98) | 3.91 (3.87) | 9.59 (9.64) | 7.50-6.90(m, 7H), 5.20(s, 2H), 3.95(s, 2H), 2.98-2.80(m, 3H), 1.33(t, 3H) |
| 17 | 4-((CH₃CH₂)₂NC(=O))-C₆H₄-CH₂- | 1 | Cl | Cl | oil | 58.07 (58.15) | 4.87 (4.80) | 9.67 (9.63) | 7.30-6.60(m, 7H), 5.20(s, 2H), 4.00(s, 2H), 3.35(q, 4H), 1.28(t, 6H) |
| 18 | thiophene-CH₂- | 1 | Cl | Cl | oil | 49.28 (49.38) | 2.95 (3.01) | 8.21 (8.09) | 7.30-6.60(m, 6H), 5.20(s, 2H), 4.20(s, 2H) |
| 19 | FCH₂- | 1 | Cl | Cl | mp 63-64° C. | 43.33 (43.28) | 2.53 (2.58) | 10.11 (10.04) | 7.38-6.73(m, 3H), 5.47(d, 2H), 5.32(s, 2H) |
| 20 | ClCH₂- | 1 | Cl | Cl | mp 65-66° C. | 40.92 (40.97) | 2.4 (2.48) | 9.54 (9.47) | 7.30-6.80(m, 3H), 5.25(s, 2H), 4.55(s, 2H) |
| 21 | BrCH₂- | 1 | Cl | Cl | oil | 35.51 (35.45) | 2.07 (2.01) | 8.29 (8.35) | 7.45-6.81(m, 3H), 5.32(s, 2H), 4.42(s, 2H) |
| 22 | HOCH₂- | 1 | Cl | Cl | mp 76-77° C. | 43.70 (43.83) | 2.91 (2.87) | 10.19 (10.24) | 7.48-6.79(m, 3H), 5.38(s, 2H), 4.73(s, 2H), 3.82(bs, 1H) |
| 23 | 4-F-C₆H₄-OCH₂- | 1 | Cl | Cl | oil | 52.04 (51.98) | 2.98 (2.93) | 7.59 (7.55) | 7.32-6.62(m, 7H), 5.38(s, 2H), 5.22(s, 2H) |

TABLE 1-continued

![structure: R-C(=N-O-(CH2)n-O-Ar(X)(Y))-N heterocycle]

| Compound No. | R | n | X | Y | Physical properties | Element analysis (%) Calculated value (Measured value) C | H | N | NMR (δ, ppm) |
|---|---|---|---|---|---|---|---|---|---|
| 24 | 2-Cl, 4-F-phenyl-OCH2— | 1 | Cl | Cl | mp 78–79° C. | 47.60 (47.68) | 2.48 (2.41) | 6.94 (6.99) | 7.34–6.54(m, 6H), 5.43(s, 2H), 5.23(s, 2H) |
| 25 | 2,4-diF-phenyl-OCH2— | 1 | Cl | Cl | mp 54–55° C. | 49.63 (49.55) | 2.58 (2.63) | 7.24 (7.21) | 7.34–6.56(m, 6H), 5.43(s, 2H), 5.22(s, 2H) |
| 26 | 2-F-phenyl-OCH2— | 1 | Cl | Cl | oil | 50.67 (50.83) | 2.90 (2.79) | 7.39 (7.30) | 7.30–6.71(m, 7H), 5.21(s, 2H), 5.11(s, 2H) |
| 27 | 2-F, 4-Cl-phenyl-OCH2— | 1 | Cl | Cl | mp 57–59° C. | 47.60 (47.42) | 2.48 (2.57) | 6.94 (6.99) | 7.34–6.71(m, 7H), 5.20(s, 2H), 5.12(s, 2H) |
| 28 | 4-Cl-phenyl-OCH2— | 1 | Cl | Cl | mp 87–88° C. | 49.82 (49.97) | 2.85 (2.88) | 7.27 (7.32) | 7.32–6.62(m, 7H), 5.44(s, 2H), 5.24(s, 2H) |
| 29 | 5-Cl-pyridin-2-yl-OCH2— | 1 | Cl | Cl | oil | 46.00 (46.19) | 3.86 (3.81) | 10.72 (10.79) | 7.70–6.30(m, 6H), 5.40(s, 2H), 5.22(s, 2H) |

TABLE 1-continued

[Structure: R-C(=N-O-(CH₂)ₙ-O-phenyl(X,Y))]

| Compound No. | R | n | X | Y | Physical properties | Element analysis (%) Calculated value (Measured value) C | H | N | NMR (δ, ppm) |
|---|---|---|---|---|---|---|---|---|---|
| 30 | CH₃COCH₂— (C=O) | 1 | Cl | Cl | mp 52–53° C. | 45.44 (45.37) | 3.16 (3.09) | 8.84 (8.89) | 7.31–6.79(m, 3H), 5.28(s, 2H), 5.19(s, 3H), 2.21(s, 3H) |
| 31 | CH₃CH₂NHCOCH₂— (C=O) | 1 | Cl | Cl | mp 61–62° C. | 45.10 (45.24) | 3.76 (3.72) | 12.14 (12.19) | 7.31–7.12(m, 3H), 6.38(bs, 1H), 5.38(s, 2H), 5.12(s, 2H), 3.24(q, 2H), 1.23(t, 3H) |
| 32 | [4-(4-nitrophenoxy)phenyl]COCH₂— | 1 | Cl | Cl | oil | 53.50 (53.37) | 2.91 (2.94) | 8.14 (8.11) | 8.23–6.89(m, 11H), 5.50(s, 2H), 5.48(s, 2H) |
| 33 | (CH₃)₂NCOCH₂— (C=O) | 1 | Cl | Cl | mp 118–119° C. | 45.10 (45.25) | 3.76 (3.79) | 12.14 (12.09) | 7.52–7.23(m, 3H), 5.62(s, 2H), 5.15(s, 2H), 2.98(s, 6H) |
| 34 | CH₃SO₂CH₂— | 1 | Cl | Cl | mp 69–70° C. | 37.40 (37.48) | 2.83 (2.86) | 7.93 (7.88) | 7.32–6.75(m, 3H), 5.22(s, 2H), 5.20(s, 2H), 3.12(s, 3H) |
| 35 | ClCH₂COCH₂— (C=O) | 1 | Cl | Cl | mp 54–55° C. | 40.98 (40.83) | 2.56 (2.57) | 7.97 (7.92) | 7.38–6.75(m, 3H), 5.43(s, 2H), 5.42(s, 2H), 4.82(s, 2H) |
| 36 | Cl₂CHCOCH₂— (C=O) | 1 | Cl | Cl | oil | 37.33 (37.28) | 2.07 (2.11) | 7.26 (7.29) | 7.32–6.83(m, 3H), 5.98(s, 1H), 5.43(s, 2H), 5.12(s, 2H) |
| 37 | CH₃CH₂OCOCOCH₂— (two C=O) | 1 | Cl | Cl | oil | 44.81 (44.97) | 3.20 (3.26) | 7.47 (7.51) | 7.32–6.75(m, 3H), 5.43(s, 2H), 5.21(s, 2H), 4.21(q, 2H), 1.23(t, 3H) |

TABLE 1-continued

Structure:
R-C(=N-O-(CH₂)ₙ-O-Ar(X)(Y))

| Compound No. | R | n | X | Y | Physical properties | Element analysis (%) Calculated value (Measured value) C | H | N | NMR (δ, ppm) |
|---|---|---|---|---|---|---|---|---|---|
| 38 | 2,4-Cl₂-C₆H₃-OCH₂COCH₂- | 1 | Cl | Cl | oil | 45.25 (43.49) | 2.51 (2.48) | 5.86 (5.92) | 7.64–6.23(m, 6H), 5.31(s, 2H), 5.30(s, 2H), 4.78(s, 2H) |
| 39 | ClCH₂CH₂NHCOCH₂- | 1 | Cl | Cl | mp 99–101° C. | 41.01 (40.88) | 3.15 (3.08) | 11.04 (11.10) | 7.42–6.81(m, 3H), 6.12(bs, 1H), 5.21(s, 2H), 5.20(s, 2H), 3.42 (t, 4H) |
| 40 | CH₃NHCH₂- | 1 | Cl | Cl | mp 133–134° C. | 45.85 (45.98) | 3.85 (3.79) | 14.58 (14.64) | 7.30–6.70(m, 3H), 5.20(s, 2H), 3.85(s, 2H), 2.45(s, 3H), 2.20(bs, 1H) |
| 41 | CH₃CH₂NHCH₂- | 1 | Cl | Cl | oil | 47.70 (47.98) | 4.34 (4.38) | 13.91 (13.83) | 7.30–6.70(m, 3H), 5.20(s, 2H), 3.85(s, 2H), 2.60(q, 2H), 2.10(bs, 1H), 1.15(t, 3H) |
| 42 | (CH₃CH₂)₂NCH₂- | 1 | Cl | Cl | oil | 50.92 (50.85) | 5.19 (5.22) | 12.73 (12.78) | 7.30–6.70(m, 3H), 5.20(s, 2H), 3.85(s, 2H), 2.68(q, 4H), 1.05(t, 6H) |
| 43 | 4-F-C₆H₄-NHCH₂- | 1 | Cl | Cl | oil | 52.19 (52.04) | 3.26 (3.19) | 11.42 (11.70) | 7.30–6.40(m, 7H), 5.20(s, 2H), 4.37(s, 2H), 3.37(bs, 1H) |
| 44 | (2-oxopyrrolidin-1-yl)CH₂- | 1 | Cl | Cl | mp 98–99° C. | 49.14 (49.29) | 3.83 (3.89) | 12.28 (12.34) | 7.41–6.80(m, 3H), 5.20(s, 2H), 4.65(s, 2H), 3.33(t, 2H), 2.50–2.05(m, 4H) |
| 45 | C₆H₅-S(O)₂-N(CH₃)CH₂- | 1 | Cl | Cl | oil | 53.70 (53.85) | 3.98 (3.91) | 11.05 (11.12) | 7.80–6.74(m, 8H), 5.20(s, 2H), 4.52(s, 2H), 2.95(s, 3H) |

TABLE 1-continued
| Compound No. | R | n | X | Y | Physical properties | Element analysis (%) Calculated value (Measured value) | | | NMR (δ, ppm) |
|---|---|---|---|---|---|---|---|---|---|
| | | | | | | C | H | N | |
| 46 | 4-Cl-C6H4-S(O)2-N(C3H7)-CH2- | 1 | Cl | Cl | oil | 46.50 (46.54) | 3.70 (3.78) | 8.56 (8.61) | 7.62–6.85(m, 7H), 5.21(s, 2H), 4.50(s, 2H), 3.36(t, 2H), 1.80–1.62(m, 2H), 1.16(t, 3H) |
| 47 | (tetrahydrophthalimido)-CH2- | 1 | Cl | Cl | oil | 52.96 (52.89) | 3.70 (3.74) | 10.29 (10.33) | 7.32–6.85(m, 3H), 6.81(m, 2H), 5.23(s, 2H), 4.70(s, 2H), 3.18(m, 2H), 2.40(m, 4H) |
| 48 | 4-Cl-C6H4-S(O)2-N(CH2CH=CH2)-CH2- | 1 | Cl | Cl | oil | 46.69 (46.82) | 3.30 (3.29) | 8.59 (8.54) | 7.85–6.83(m, 7H), 5.81–4.90 (m, 5H), 4.52(s, 2H), 3.84(d, 2H) |
| 49 | (CH3CH2O)2P(S)S-CH2- | 1 | Cl | Cl | oil | 37.93 (37.77) | 3.87 (3.81) | 6.32 (6.38) | 7.50–6.90(m, 3H), 5.35(s, 2H), 4.80–4.10(m, 6H), 1.35(t, 6H) |
| 50 | C6H5-SCH2- | 1 | Cl | Cl | oil | 52.33 (52.18) | 3.27 (3.20) | 7.63 (7.77) | 7.41–6.72(m, 8H), 5.20(s, 2H), 4.08(s, 2H) |
| 51 | C6H5-S(O)2-CH2- | 1 | Cl | Cl | mp 75–76° C. | 48.13 (48.25) | 3.01 (3.11) | 7.02 (6.90) | 7.87–6.80(m, 8H), 5.31(s, 2H), 4.58(s, 2H) |
| 52 | (CH3CH2)2NC(O)SCH2- | 1 | Cl | Cl | oil | 46.16 (46.33) | 4.39 (4.40) | 10.77 (10.79) | 7.30–6.85(m, 3H), 5.25(s, 2H), 4.15(s, 2H), 3.28(q, 4H), 1.05(t, 6H) |

TABLE 1-continued structure: R-C(=N-O-(CH2)n-O-Ar(X)(Y))

| Compound No. | R | n | X | Y | Physical properties | C Calculated (Measured) | H Calculated (Measured) | N Calculated (Measured) | NMR (δ, ppm) |
|---|---|---|---|---|---|---|---|---|---|
| 53 | H2NNHCCH2— (with C=O) | 1 | Cl | Cl | mp 120–122° C. | 41.65 (41.53) | 3.16 (3.10) | 17.67 (17.80) | 7.31–6.90(m, 3H), 5.30–4.91 (m, 5H), 4.28(s, 2H) |
| 54 | CH3CH2OCCH2— (with C=O) | 1 | Cl | Cl | mp 35–36° C. | 47.15 (47.22) | 3.65 (3.73) | 8.46 (8.39) | 7.35–6.95(m, 3H), 5.30(s, 2H), 4.15(q, 2H), 3.75(s, 2H), 1.20(t, 3H) |
| 55 | phenyl | 1 | Cl | Cl | mp 100–101° C. | 56.10 (56.37) | 3.14 (3.12) | 8.72 (8.83) | 8.10–7.80(m, 2H), 7.40–6.90 (m, 6H), 5.30(s, 2H) |
| 56 | 2-Cl-phenyl | 1 | Cl | Cl | mp 79–80° C. | 50.67 (50.78) | 2.55 (2.52) | 7.88 (7.81) | 7.90–7.70(m, 1H), 7.40–6.90 (m, 6H), 5.20(s, 2H) |
| 57 | 2-F-6-Cl-phenyl | 1 | Cl | Cl | mp 98–99° C. | 48.23 (48.47) | 2.16 (2.18) | 7.50 (7.54) | 7.30–6.90(m, 6H), 5.34(s, 2H) |
| 58 | 3-CF3-phenyl | 1 | Cl | Cl | oil | 49.38 (49.48) | 2.33 (2.30) | 7.20 (7.17) | 8.30–8.10(m, 2H), 7.50–6.90 (m, 5H), 5.30(s, 2H) |

TABLE 1-continued

[Structure: R-C(=N-O-(CH₂)n-O-phenyl(X)(Y))]

| Compound No. | R | n | X | Y | Physical properties | Element analysis (%) Calculated value (Measured value) C | H | N | NMR (δ, ppm) |
|---|---|---|---|---|---|---|---|---|---|
| 59 | 2,4-di(CH₃O)-phenyl | 1 | Cl | Cl | mp 79-81° C. | 53.56 (53.69) | 3.70 (3.73) | 7.35 (7.31) | 7.50-6.70(m, 6H), 5.25(s, 2H), 3.80(s, 6H) |
| 60 | 2-pyridyl | 1 | Cl | Cl | mp 104-105° C. | 52.19 (52.28) | 2.82 (2.79) | 14.04 (14.01) | 8.70-8.50(m, 1H), 8.00-6.80 (m, 6H), 5.30(s, 2H) |
| 61 | 2-methylthienyl | 1 | Cl | Cl | mp 94-95° C. | 47.72 (47.88) | 2.46 (2.43) | 8.56 (8.52) | 7.80-6.80(m, 6H), 5.30(s, 2H) |
| 62 | 1,5-dimethylpyrrol-2-yl | 1 | Cl | Cl | mp 91-92° C. | 53.27 (53.04) | 3.87 (3.84) | 12.42 (12.48) | 7.25-7.06(m, 3H), 6.60(d, 1H), 5.75(d, 1H), 5.40(s, 2H), 3.75(s, 3H), 2.20(s, 3H) |
| 63 | CH=CH₂—phenyl | 1 | Cl | Cl | mp 120-121° C. | 58.81 (58.66) | 3.49 (3.45) | 8.07 (8.10) | 7.60-6.80(m, 10H), 5.30(s, 2H) |
| 64 | CH₃CH₂O— | 1 | Cl | Cl | mp 96-97° C. | 45.70 (45.98) | 3.49 (3.41) | 9.69 (9.74) | 7.35-6.80(m, 3H), 5.15(s, 2H), 4.33(8, 2H), 1.48(t, 3H) |
| 65 | CH₃CH₂CH₂O— | 1 | Cl | Cl | mp 78-79° C. | 47.54 (47.37) | 3.96 (3.91) | 9.24 (9.32) | 7.50-7.20(m, 3H), 5.38(s, 2H), 4.17(t, 2H), 1.90-1.32(m, 2H), 0.58(t, 3H) |

TABLE 1-continued

R–C(=N–O–(CH2)n–phenyl(X,Y))

| Compound No. | R | n | X | Y | Physical properties | Element analysis (%) Calculated value (Measured value) C | H | N | NMR (δ, ppm) |
|---|---|---|---|---|---|---|---|---|---|
| 66 | phenyl | 1 | Cl | Cl | mp 94–95° C. | 53.44 (53.57) | 2.99 (3.07) | 8.31 (8.37) | 7.40–7.10(m, 8H), 5.35(s, 2H) |
| 67 | 4-Cl-phenyl | 1 | Cl | Cl | mp 97–98° C. | 48.48 (48.58) | 2.44 (2.48) | 7.54 (7.46) | 7.40–6.90(m, 7H), 5.25(s, 2H) |
| 68 | 2,4-diCl-phenyl | 1 | Cl | Cl | mp 75–76° C. | 44.37 (44.49) | 1.99 (1.92) | 6.90 (6.86) | 7.42–6.77(m, 6H), 5.23(s, 2H) |
| 69 | 4-F-phenyl | 1 | Cl | Cl | mp 70–71° C. | 50.73 (50.96) | 2.55 (2.58) | 7.89 (7.82) | 7.50–6.82(m, 7H), 5.21(s, 2H) |
| 70 | 2-Cl-4-F-phenyl | 1 | Cl | Cl | mp 81–82° C. | 46.25 (46.41) | 2.07 (2.13) | 7.19 (7.23) | 7.40–6.80(m, 6H), 5.19(s, 2H) |
| 71 | 2,4-diF-phenyl | 1 | Cl | Cl | mp 59–60° C. | 48.28 (28.52) | 2.16 (2.09) | 7.51 (7.54) | 7.42–6.82(m, 6H), 5.31(s, 2H) |

TABLE 1-continued

Structure:
R-C(=N-O-(CH2)n-O-C6H3(X)(Y))

| Compound No. | R | n | X | Y | Physical properties | Element analysis (%) Calculated value (Measured value) | | | NMR (δ, ppm) |
|---|---|---|---|---|---|---|---|---|---|
| | | | | | | C | H | N | |
| 72 | 2-fluorophenoxy | 1 | Cl | Cl | mp 84–85° C. | 50.72 (50.61) | 2.54 (2.48) | 7.89 (7.95) | 7.40–6.82(m, 7H), 5.20(s, 2H) |
| 73 | 4-chloro-2-fluorophenoxy | 1 | Cl | Cl | mp 58–59° C. | 46.23 (46.10) | 2.05 (2.00) | 7.19 (7.27) | 7.40–6.80(m, 6H), 5.21(s, 2H) |
| 74 | CH3CH2OCCH(CH3)O-phenoxy | 1 | Cl | Cl | mp 43–44° C. | 53.00 (53.35) | 4.00 (4.01) | 6.18 (6.14) | 7.40–6.80(m, 7H), 5.25(s, 2H), 4.75(q, 1H), 4.25(q, 2H), 1.65(d, 3H), 1.30(t, 3H) |
| 75 | H2N— | 1 | Cl | Cl | mp 175–176° C. | 41.56 (71.71) | 2.71 (2.80) | 16.16 (16.27) | 7.45–7.05(m, 3H), 5.05(s, 2H), 2.85(s, 2H) |
| 76 | piperidin-1-yl | 1 | Cl | Cl | mp 75–76° C. | 51.24 (54.38) | 4.61 (4.58) | 12.80 (12.77) | 7.25–6.85(m, 3H), 5.01(s, 2H), 3.30(m, 4H), 1.55(m, 6H) |
| 77 | CH3CNH—C(=O)— | 1 | Cl | Cl | mp 118–119° C. | 43.73 (43.89) | 3.01 (2.98) | 13.90 (13.99) | 7.45–7.20(m, 3H), 5.25(s, 2H), 2.85(bs, 1H), 2.30(s, 3H) |
| 78 | CH3OCNH—C(=O)— | 1 | Cl | Cl | mp 90–91° C. | 41.53 (41.47) | 2.85 (2.90) | 13.21 (13.23) | 7.65(bs, 1H), 7.60–7.20(m, 3H), 5.65(s, 2H), 4.01(s, 3H) |
| 79 | CH3CH2OCNH—C(=O)— | 1 | Cl | Cl | mp 136–137° C. | 43.39 (43.48) | 3.34 (3.48) | 12.65 (12.58) | 7.30–6.90(m, 4H), 5.30(s, 2H), 4.10(q, 2H), 1.25(t, 3H) |

TABLE 1-continued

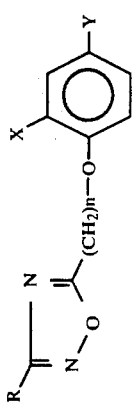

| Compound No. | R | n | X | Y | Physical properties | Element analysis (%) Calculated value (Measured value) C | H | N | NMR (δ, ppm) |
|---|---|---|---|---|---|---|---|---|---|
| 80 | (CH₃)₂NCNH— (with C=O) | 1 | Cl | Cl | mp 93–94° C. | 43.54 (43.31) | 3.65 (3.69) | 16.92 (16.90) | 9.60(bs, 1H), 7.60–7.20(m, 3H), 5.50(s, 2H), 2.90(s, 6H) |
| 81 | CH₃NHCNH— (with C=O) | 1 | Cl | Cl | mp 208–210° C. | 41.66 (41.42) | 3.50 (3.41) | 17.67 (17.81) | 7.90(bs, 1H), 7.50–7.10(m, 4H), 5.25(s, 2H), 3.22(d, 3H) |
| 82 | HCNH— (with C=O) | 1 | Cl | Cl | mp 57–58° C. | 41.69 (41.93) | 2.45 (2.44) | 14.59 (14.56) | 8.78(s, 1H), 7.28–6.81(m, 4H), 5.19(s, 2H) |
| 83 | phenyl-S(=O)(=O)-N(CH₃)— | 1 | Cl | Cl | mp 122–123° C. | 46.39 (46.57) | 3.16 (3.21) | 10.14 (10.19) | 8.02–6.83(m, 8H), 5.20(s, 2H), 3.42(s, 3H) |
| 84 | (CH₃)₂NCH=N— | 1 | Cl | Cl | oil | 45.73 (15.90) | 3.84 (3.85) | 17.78 (17.74) | 8.51(s, 1H), 7.37–6.99(m, 3H), 5.14(s, 2H), 3.21(s, 3H), 3.10(s, 3H) |
| 85 | CH₃CH₂OC=N— / CH₃ | 1 | Cl | Cl | mp 70–71° C. | 47.29 (47.52) | 3.97 (3.99) | 12.73 (12.78) | 7.31–6.90(m, 3H), 5.12(s, 2H), 4.30(q, 2H), 2.21(s, 2H), 1.30(t, 3H) |
| 86 | CH₃CH₂OC=N— / CH₂CH₃ | 1 | Cl | Cl | mp 65–66° C. | 48.85 (48.80) | 4.39 (4.39) | 12.21 (12.23) | 7.30–6.80(m, 3H), 5.12(s, 2H), 4.78(q, 2H), 2.53(q, 2H), 1.16(m, 6H) |
| 87 | 2-F-C₆H₄-NHCH=N— | 1 | Cl | Cl | mp 161–162° C. | 50.41 (50.49) | 2.91 (2.92) | 14.70 (14.68) | 8.68–8.61(d, 1H), 7.45–6.93 (m, 7H), 5.10(s, 2H), 4.92(d, 1H) |
| 88 | phenyl-S(=O)(=O)— | 1 | Cl | Cl | mp 140–141° C. | 46.77 (46.52) | 2.60 (2.69) | 7.27 (7.11) | 7.45–6.74(m, 8H), 5.32(s, 2H) |

TABLE 1-continued

![Structure: R-C(=N-O-(CH2)n-O-phenyl with X and Y substituents)]

| Compound No. | R | n | X | Y | Physical properties | Element analysis (%) Calculated value (Measured value) | | | NMR (δ, ppm) |
|---|---|---|---|---|---|---|---|---|---|
| | | | | | | C | H | N | |
| 89 | Cl— | 1 | Cl | Cl | mp 58–59° C. | 38.67 (38.50) | 1.80 (1.86) | 15.03 (15.01) | 7.40–7.15(m, 3H), 5.45(s, 2H) |
| 90 | Br— | 1 | Cl | Cl | mp 62–63° C. | 44.28 (44.16) | 2.05 (2.01) | 11.48 (11.39) | 7.38–7.15(m, 3H), 5.40(s, 2H) |
| 91 | CH₃NHCN(O)—CH₃ | 1 | Cl | Cl | mp 99–101° C. | 43.52 (42.61) | 3.65 (3.69) | 16.92 (16.87) | 8.70(bs, 1H), 7.35–7.15(m, 3H), 5.22(s, 2H), 3.35(s, 3H), 2.90(d, 3H) |
| 92 | (CH₃)₂NCN(O)—CH₃ | 1 | Cl | Cl | mp 74–75° C. | 45.23 (45.31) | 4.09 (4.11) | 16.23 (16.29) | 7.40–7.42(m, 3H), 5.25(s, 2H), 3.32(s, 3H), 3.02(s, 6H) |
| 93 | CH₃OC(O)— | 1 | Cl | Cl | mp 110–112° C. | 43.59 (43.40) | 2.66 (2.59) | 9.24 (9.37) | 7.51–7.20(m, 3H), 5.62(s, 2H), 3.89(s, 3H) |
| 94 | CH₃CH₂OC(O)— | 1 | Cl | Cl | mp 94–95° C. | 45.45 (45.37) | 3.18 (3.21) | 8.83 (8.78) | 7.30–6.80(m, 3H), 5.30(s, 2H), 4.48(q, 2H), 1.45(t, 3H) |
| 95 | CH₃NHC(O)— | 1 | Cl | Cl | mp 162–163° C. | 43.73 (43.85) | 3.00 (3.01) | 13.91 (13.88) | 8.80(bs, 1H), 7.50–7.20(m, 3H), 5.60(s, 2H), 2.88(d, 3H) |
| 96 | CH₃CH₂CH₂CH₂NHC(O)— | 1 | Cl | Cl | mp 90–91° C. | 48.85 (48.97) | 4.36 (4.32) | 12.21 (12.30) | 7.30–6.90(m, 3H), 5.40(s, 2H), 3.50(t, 2H), 1.70–1.30(m, 5H), 1.05(t, 3H) |
| 97 | CH₂=CHCH₂NHC(O)— | 1 | Cl | Cl | mp 110–111° C. | 47.58 (47.42) | 3.35 (3.34) | 12.81 (12.92) | 7.50–7.00(m, 5H), 5.40–5.20 (m, 4H), 4.40–4.00(m, 2H) |
| 98 | H₂NNHC(O)— | 1 | Cl | Cl | mp 105–106° C. | 39.63 (36.89) | 2.67 (2.68) | 18.48 (17.37) | 7.45–7.10(m, 3H), 6.10(bs, 3H), 5.50(s, 2H) |

TABLE 1-continued

| Compound No. | R | n | X | Y | Physical properties | Element analysis (%) Calculated value (Measured value) | | | NMR (δ, ppm) |
|---|---|---|---|---|---|---|---|---|---|
| | | | | | | C | H | N | |
| 99 | (CH₃CH₂)₂NC(=O)— | 1 | Cl | Cl | mp 104–106° C. | 48.85 (48.77) | 4.40 (4.38) | 12.20 (12.25) | 7.50–7.10(m, 3H), 5.45(s, 2H), 3.55(q, 4H), 1.25(t, 6H) |
| 100 | (CH₃)₂NC(=O)— | 1 | Cl | Cl | mp 114–115° C. | 45.59 (45.64) | 3.51 (3.48) | 13.29 (13.32) | 7.60–7.30(m, 3H), 5.65(s, 2H), 3.05(s, 6H) |
| 101 | (CH₃O)NC(=O)—CH₃ | 1 | Cl | Cl | mp 68–70° C. | 43.39 (43.16) | 3.35 (3.32) | 12.65 (12.61) | 7.41–6.70(m, 3H), 5.32(s, 2H), 3.70(s, 3H), 3.31(s, 3H) |
| 102 | CH₃CH₂CH₂NHC(=O)— | 1 | Cl | Cl | mp 116–118° C. | 47.29 (47.38) | 3.97 (4.02) | 12.73 (12.65) | 7.60–7.35(m, 3H), 5.65(s, 2H), 3.38(q, 2H), 1.90–7.40(m, 2H), 0.98(t, 3H) |
| 103 | H₂NC(=O)— | 1 | Cl | Cl | mp 173–175° C. | 41.69 (41.64) | 2.45 (2.47) | 14.59 (14.62) | 7.90(bs, 2H), 7.60–7.30(m, 3H), 5.65(s, 2H) |
| 104 | N₃C(=O)— | 1 | Cl | Cl | mp 103–104° C. | 38.24 (38.47) | 1.61 (1.58) | 22.29 (22.35) | 7.45–7.15(m, 3H), 5.25(s, 2H) |
| 105 | 4-Cl-pyridin-2-yl-NHC(=O)— | 1 | Cl | Cl | mp 132–133° C. | 45.08 (45.21) | 2.27 (2.29) | 14.02 (14.05) | 9.85(bs, 1H), 8.35–8.15(m, 2H), 7.90–7.75(m, 1H), 7.55–7.45(m, 1H), 7.45–7.20(m, 2H), 4.90(s, 2H) |
| 106 | C₆H₅NHC(=O)— | 1 | Cl | Cl | mp 157–158° C. | 52.77 (52.88) | 3.05 (3.03) | 11.53 (11.49) | 10.45(bs, 1H), 7.90–7.05(m, 8H), 5.50(s, 2H) |
| 107 | 4-F-C₆H₄-NHC(=O)— | 1 | Cl | Cl | mp 142–143° C. | 50.28 (50.38) | 2.64 (2.67) | 10.99 (10.90) | 10.5(bs, 1H), 7.90–6.85(m, 7H), 5.62(s, 2H) |

TABLE 1-continued

Structure:

R−C(=N−O−(CH₂)ₙ−)−[phenyl with X, Y substituents]

| Compound No. | R | n | X | Y | Physical properties | Element analysis (%) Calculated value (Measured value) C | H | N | NMR (δ, ppm) |
|---|---|---|---|---|---|---|---|---|---|
| 108 | 4-Cl-C₆H₄-NHC(=O)- | 1 | Cl | Cl | mp 152-153° C. | 48.21 (48.45) | 2.53 (2.57) | 10.54 (10.60) | 10.4(bs, 1H), 7.80-7.05(m, 7H), 5.45(s, 2H) |
| 109 | CH₃C(=O)NHC(=O)- | 1 | Cl | Cl | mp 128-129° C. | 43.66 (43.80) | 2.75 (2.72) | 12.72 (12.68) | 7.39-7.28(m, 3H), 5.60(s, 2H), 4.75(bs, 1H), 2.42(s, 3H) |
| 110 | CH₃S(=O)₂NHC(=O)- | 1 | Cl | Cl | mp 175-176° C. | 36.09 (36.01) | 2.48 (2.50) | 11.47 (11.53) | 7.97(bs, 1H), 7.48-7.25(m, 3H), 5.60(s, 2H), 3.18(s, 3H) |
| 111 | CH₃C(=O)- | 1 | Cl | Cl | mp 118-119° C. | 46.02 (46.17) | 2.81 (2.75) | 9.76 (9.68) | 7.32-6.81(m, 3H), 5.27(s, 2H), 2.72(s, 3H) |
| 112 | CH₃CH₂C(=O)- | 1 | Cl | Cl | mp 115-116° C. | 47.86 (47.62) | 3.35 (3.28) | 9.30 (9.16) | 7.30-6.82(m, 3H), 5.31(s, 2H), 3.08(q, 2H), 1.16(t, 3H) |
| 113 | CH₃CH₂CH₂C(=O)- | 1 | Cl | Cl | mp 54-56° C. | 49.54 (49.39) | 3.84 (3.74) | 8.89 (8.96) | 7.31-6.80(m, 3H), 5.30(s, 2H), 3.17(t, 2H), 1.90-1.50(m, 2H), 1.06(t, 3H) |
| 114 | CH₃CH₂CH₂CH₂C(=O)- | 1 | Cl | Cl | mp 60-62° C. | 51.08 (50.91) | 4.29 (4.20) | 8.51 (8.42) | 7.32-6.80(m, 3H), 5.31(s, 2H), 3.06(t, 2H), 1.70-1.22(m, 4H), 0.98(t, 3H) |
| 115 | CH₃CH₂CHC(=O)-  \|  CH₃ | 1 | Cl | Cl | mp 112-113° C. | 51.08 (50.87) | 4.29 (4.18) | 8.51 (8.45) | 7.28-6.81(m, 3H), 5.29(s, 2H), 3.30-2.90(m, 1H), 1.80-1.20(m, 5H), 0.97(t, 3H) |

TABLE 1-continued $$R-C(=N-O-(CH_2)_n-O-C_6H_3(X)(Y))$$

| Compound No. | R | n | X | Y | Physical properties | Element analysis (%) Calculated value (Measured value) C | H | N | NMR (δ, ppm) |
|---|---|---|---|---|---|---|---|---|---|
| 116 | C₆H₅-CH₂-C(=O)- | 1 | Cl | Cl | mp 94–96° C. | 56.22 (56.01) | 3.33 (3.27) | 7.71 (7.80) | 7.70–6.81(m, 8H), 5.30(s, 2H), 3.88(s, 2H) |
| 117 | C₆H₅-C(=O)- | 1 | Cl | Cl | mp 81–82° C. | 55.04 (55.21) | 2.89 (2.80) | 8.02 (8.17) | 8.10–7.22(m, 8H), 5.72(s, 2H) |
| 118 | CH₃-C(=N-OH)- | 1 | Cl | Cl | mp 163–164° C. | 43.72 (43.88) | 2.98 (2.91) | 13.91 (13.95) | 12.02(s, 1H), 7.23–7.20(m, 3H), 5.69(s, 2H), 2.32(s, 3H) |
| 119 | CH₃CH₂-C(=N-OH)- | 1 | Cl | Cl | mp 126–127° C. | 45.58 (45.45) | 3.48 (3.53) | 13.30 (13.28) | 12.02(s, 1H), 7.23–7.18(m, 3H), 5.65(s, 2H), 2.75(q, 2H), 1.23 (t, 3H) |
| 120 | CH₃CH₂CH₂-C(=N-OH)- | 1 | Cl | Cl | mp 139–140° C. | 47.29 (47.37) | 3.94 (3.97) | 12.73 (12.68) | 12.10(s, 1H), 7.23–7.20(m, 3H), 5.42(s, 2H), 2.82(t, 2H), 1.68(m, 2H), 1.01(t, 3H) |
| 121 | CH₃CH₂CH₂CH₂-C(=N-OH)- | 1 | Cl | Cl | mp 110–112° C. | 48.85 (48.71) | 4.36 (4.32) | 12.21 (12.27) | 12.23(s, 1H), 7.29–7.25(m, 3H), 5.42(s, 2H), 2.81(t, 2H), 1.53(m, 4H), 0.98(t, 3H) |
| 122 | C₆H₅-C(=N-OH)- | 1 | Cl | Cl | mp 155–156° C. | 52.76 (52.57) | 3.02 (3.05) | 11.54 (11.50) | 12.23(s, 1H), 7.28–7.24(m, 3H), 5.62(s, 2H) |
| 123 | CH₃CH₂-C(=N-OCH₂CH₃)- | 1 | Cl | Cl | mp 80–81° C. | 48.85 (48.60) | 4.39 (4.45) | 12.21 (12.15) | 7.30–6.82(m, 3H), 5.30(s, 2H), 4.15(q, 2H), 1.40–1.02(m, 6H) |
| 124 | CH₃CH₂CH₂-C(=N-OCH₂CH₃)- | 1 | Cl | Cl | oil | 50.29 (50.12) | 4.78 (4.70) | 11.74 (11.62) | 7.30–6.82(m, 3H), 5.30(s, 2H), 4.16(q, 2H), 2.75(t, 2H), 1.72–0.82(m, 8H) |

TABLE 1-continued

Structure:
$$R-C(=N-O-(CH_2)_n-)-\text{phenyl}(X,Y)$$

| Compound No. | R | n | X | Y | Physical properties | Element analysis (%) Calculated value (Measured value) C | H | N | NMR (δ, ppm) |
|---|---|---|---|---|---|---|---|---|---|
| 125 | CH$_3$OC(=NH)— | 1 | Cl | Cl | mp 98–100° C. | 43.73 (43.60) | 3.00 (3.07) | 13.91 (13.80) | 8.92(bs, 1H), 7.42–7.19(m, 3H), 5.58(s, 2H), 3.80(s, 3H) |
| 126 | CH$_3$CH$_2$OC(=NH)— | 1 | Cl | Cl | mp 84–86° C. | 45.59 (45.74) | 3.51 (3.48) | 15.18 (15.11) | 9.15–8.85(bs, 1H), 7.55–7.25 (m, 3H), 5.60(s, 2H), 3.75(q, 2H), 1.20(t, 3H) |
| 127 | HONHC(=NH)— | 1 | Cl | Cl | mp 138–139° C. | 39.63 (39.78) | 2.67 (2.68) | 18.48 (18.45) | 9.70(bs, 1H), 7.50–7.20(m, 3H), 5.50(s, 2H), 2.88(bs, 2H) |
| 128 | H$_2$NC(=NH)— | 1 | Cl | Cl | mp 168–169° C. | 41.84 (41.76) | 2.81 (2.79) | 19.51 (19.55) | 7.95(bs, 1H), 7.50–7.25(m, 3H), 5.65(s, 2H), 3.30(bs, 2H) |
| 129 | hydantoin-like ring | 1 | Cl | Cl | mp 139–140° C. | 42.25 (42.39) | 1.78 (1.80) | 16.42 (16.46) | 8.70(bs, 1H), 7.40–7.15(m, 3H), 5.35(s, 2H) |
| 130 | CH$_3$OC(=NCl)— | 1 | Cl | Cl | mp 97–99° C. | 39.26 (39.39) | 2.40 (2.39) | 14.26 (14.21) | 7.50–7.20(m, 3H), 5.65(s, 2H), 4.00(s, 3H) |
| 131 | CH$_3$OC(=NP(O)(OCH$_2$CH$_3$)$_2$)— | 1 | Cl | Cl | mp 103–104° C. | 41.11 (41.03) | 4.15 (4.17) | 9.58 (9.63) | 7.50–7.20(m, 3H), 5.65(s, 2H), 3.95(q, 4H), 1.28(t, 6H) |
| 132 | epoxide-CHCH$_2$— | 1 | Cl | Cl | mp 32–33° C. | 47.86 (47.69) | 3.35 (3.36) | 9.30 (9.28) | 7.34–6.81(m, 3H), 5.25(s, 2H), 3.27–2.64(m, 5H) |
| 133 | N$_3$CH$_2$CH(OH)CH$_2$— | 1 | Cl | Cl | mp 51–52° C. | 41.87 (41.72) | 3.20 (3.27) | 20.35 (20.19) | 7.45–6.75(m, 3H), 5.22(s, 2H), 4.45–4.01(m, 1H), 3.35(d, 2H), 3.10–2.85(m, 3H) |

TABLE 1-continued structure: R-C(=N-O-(CH₂)ₙ-O-C₆H₃(X)(Y))

| Compound No. | R | n | X | Y | Physical properties | Element analysis (%) Calculated value (Measured value) C | H | N | NMR (δ, ppm) |
|---|---|---|---|---|---|---|---|---|---|
| 134 | CH₃OCH₂CHCH₂— / OH | 1 | Cl | Cl | mp 43–44° C. | 46.86 (46.94) | 4.21 (4.17) | 8.41 (8.46) | 7.41–6.75(m, 3H), 5.26(s, 2H), 4.40–4.00(m, 2H), 3.50–3.28 (m, 5H), 3.15–2.85(m, 3H) |
| 135 | Cl₃C— | 1 | Cl | Cl | mp 100–102° C. | 33.14 (33.29) | 1.39 (1.31) | 7.73 (7.61) | 7.30–6.82(m, 3H), 5.28(s, 2H) |
| 136 | OH / CH₃CH₂CH₂C— / CH₃ | 1 | Cl | Cl | mp 43–44° C. | 50.77 (50.43) | 4.87 (4.74) | 8.46 (8.54) | 7.30–6.82(m, 3H), 5.29(s, 2H), 3.02(s, 1H), 1.87(t, 2H), 1.72 (s, 3H), 1.60–1.28(m, 2H), 0.95(t, 3H) |
| 137 | OH / CH₃CH₂CH— | 1 | Cl | Cl | oil | 47.55 (47.70) | 3.99 (3.93) | 9.24 (9.17) | 7.30–6.81(m, 3H), 5.28(s, 2H), 4.76(q, 1H), 3.30(d, 1H), 1.61–1.30(m, 2H), 0.97(t, 3H) |
| 138 | OH / CH₃CH₂CH₂CH— | 1 | Cl | Cl | oil | 49.07 (48.87) | 4.75 (4.67) | 8.80 (8.63) | 7.30–6.80(m, 3H), 5.28(s, 2H), 4.85(q, 1H), 2.80(d, 1H), 1.90–1.22(m, 4H), 0.96(t, 3H) |
| 139 | OH / (CH₃)₂C— | 1 | Cl | Cl | oil | 47.55 (47.40) | 3.99 (4.07) | 9.24 (9.35) | 7.30–6.82(m, 3H), 5.29(s, 2H), 3.02(bs, 1H), 1.60(s, 6H) |
| 140 | C₆H₅CH₂— | 1 | F | Cl | oil | 60.29 (60.12) | 3.77 (3.70) | 8.79 (8.92) | 7.22–6.80(m, 8H), 5.20(s, 2H), 4.09(s, 2H) |
| 141 | 4-F-C₆H₄CH₂— | 1 | F | Cl | oil | 57.07 (7.23) | 3.27 (3.21) | 8.32 (8.15) | 7.40–6.70(m, 7H), 5.20(s, 2H), 4.02(s, 2H) |
| 142 | CH₃CH₂CH₂— | 1 | F | Cl | oil | 53.24 (53.02) | 4.44 (4.35) | 10.35 (10.27) | 7.20–6.85(m, 7H), 5.26(s, 2H), 2.66(t, 2H), 2.06–1.38(m, 2H), 0.93(t, 3H) |

TABLE 1-continued
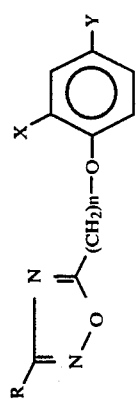
| Compound No. | R | n | X | Y | Physical properties | Element analysis (%) Calculated value (Measured value) | | | NMR (δ, ppm) |
|---|---|---|---|---|---|---|---|---|---|
| | | | | | | C | H | N | |
| 143 | C6H5CH2— | 1 | Cl | F | oil | 60.29 (60.02) | 3.77 (3.68) | 8.79 (8.87) | 7.30–6.85(m, 8H), 5.35(s, 2H), 4.05(s, 2H) |
| 144 | CH3CH2CH2— | 1 | Cl | F | oil | 53.24 (53.10) | 4.44 (4.38) | 10.35 (10.21) | 7.20–6.80(m, 7H), 5.20(s, 2H), 2.65(t, 2H), 2.06–1.35(m, 2H), 0.95(t, 3H) |
| 145 | CH2=CHCH2— | 1 | Cl | F | oil | 53.64 (53.49) | 3.73 (3.70) | 10.43 (10.48) | 7.23–6.75(m, 3H), 6.34–5.79 (m, 3H), 5.28(s, 2H), 3.58(d, 2H) |
| 146 | 4-Cl-C6H4CH2— | 1 | Cl | F | oil | 54.41 (54.48) | 2.83 (2.81) | 7.93 (7.86) | 7.32–6.72(m, 7H), 5.21(s, 2H), 4.02(s, 2H) |
| 147 | 4-F-C6H4CH2— | 1 | Cl | F | oil | 57.07 (57.30) | 2.97 (2.95) | 8.32 (8.37) | 7.32–6.62(m, 7H), 5.23(s, 2H), 4.02(s, 2H) |
| 148 | CH3CH2CH2— | 1 | CH3 | Cl | mp 44–45° C. | 58.54 (58.39) | 5.67 (5.65) | 10.50 (10.58) | 7.15–6.67(m, 3H), 5.15(s, 2H), 2.78(t, 2H), 2.24(s, 3H), 2.09–1.56(m, 2H), 1.02(t, 3H) |
| 149 | ClCH2— | 1 | CH3 | Cl | mp 30–31° C. | 48.37 (48.18) | 3.66 (3.69) | 10.26 (10.22) | 7.32–6.72(m, 3H), 5.29(s, 2H), 4.76(s, 2H), 2.25(s, 3H) |
| 150 | CH3COCH2— | 1 | CH3 | Cl | oil | 52.62 (52.75) | 4.39 (4.43) | 9.45 (9.40) | 7.32–6.72(m, 3H), 5.33(s, 2H), 5.32(s, 2H), 2.33(s, 3H), 2.31(s, 3H) |
| 151 | HOCH2— | 1 | CH3 | Cl | mp 71–72° C. | 51.88 (51.64) | 4.32 (4.35) | 11.00 (11.04) | 7.32–6.72(m, 3H), 5.32(s, 2H), 4.82(s, 2H), 4.28(bs, 1H), 2.32(s, 3H) |

TABLE 1-continued

Structure:

R-C(=N-O-(CH₂)ₙ-O-phenyl(X,Y))

| Compound No. | R | n | X | Y | Physical properties | C calc (meas) | H calc (meas) | N calc (meas) | NMR (δ, ppm) |
|---|---|---|---|---|---|---|---|---|---|
| 152 | 2-Cl-4-F-C₆H₃-OCH₂- | 1 | CH₃ | Cl | mp 64-65° C. | 53.33 (53.18) | 3.40 (3.42) | 7.31 (7.28) | 7.32-6.65(m, 6H), 5.23(s, 2H), 5.22(s, 2H), 2.32(s, 3H) |
| 153 | CH₃CH₂O- | 1 | CH₃ | Cl | mp 86-87° C. | 53.64 (53.57) | 4.88 (4.81) | 10.42 (10.47) | 7.20-6.80(m, 3H), 5.10(s, 2H), 4.33(q, 2H), 2.21(s, 3H), 1.46(t, 3H) |
| 154 | CH₃CH₂OC(=O)- | 1 | CH₃ | Cl | mp 90-91° C. | 52.62 (52.47) | 4.43 (4.42) | 9.44 (9.49) | 7.08-6.45(m, 3H), 4.45(q, 2H), 2.10(s, 3H), 1.41(t, 3H) |
| 155 | CH₃NHC(=O)- | 1 | CH₃ | Cl | mp 129-130° C. | 51.16 (51.43) | 4.30 (4.33) | 14.91 (14.95) | 7.70-7.40(bs, 1H), 7.40-6.70(m, 3H), 5.65(s, 2H), 2.78(d, 3H), 2.10(s, 3H) |
| 156 | (CH₃)₂NC(=O)- | 1 | CH₃ | Cl | mp 87-88° C. | 52.79 (52.70) | 4.78 (4.82) | 14.20 (14.15) | 7.40-6.70(m, 3H), 5.65(s, 2H), 2.90(s, 6H), 2.10(s, 3H) |
| 157 | (CH₃CH₂)₂NC(=O)- | 1 | CH₃ | Cl | mp 108-109° C. | 55.64 (55.49) | 5.61 (5.59) | 12.97 (13.00) | 7.40-6.70(m, 3H), 5.65(s, 2H), 4.03(q, 4H), 2.10(s, 3H), 1.20(t, 6H) |
| 158 | CH₃CH₂CH₂- | 3 | CH₃ | Cl | mp 31-32° C. | 64.12 (64.28) | 6.50 (6.48) | 9.50 (9.44) | 7.10-6.60(m, 3H), 3.96(t, 2H), 2.99(t, 2H), 2.80-1.62(m, 7H), 0.94(t, 3H) |
| 159 | ClCH₂- | 3 | CH₃ | Cl | oil | 51.84 (51.67) | 4.65 (4.60) | 9.31 (9.36) | 7.31-6.62(m, 3H), 4.63(s, 2H), 4.02(t, 2H), 3.17(t, 2H), 2.42-2.12(m, 5H) |
| 160 | CH₃COCH₂- | 3 | CH₃ | Cl | oil | 55.48 (55.33) | 5.24 (5.21) | 8.63 (8.65) | 7.31-6.58(m, 3H), 5.28(s, 2H), 3.98(t, 2H), 3.17(t, 2H), 2.43-2.02(m, 8H) |
| 161 | HOCH₂- | 3 | CH₃ | Cl | mp 65-66° C. | 55.28 (53.37) | 4.96 (4.95) | 9.91 (9.95) | 7.27-6.51(m, 3H), 4.73(s, 2H), 4.55(bs, 1H), 4.01(t, 2H), 3.12(t, 2H), 2.67-2.10(m, 5H) |
| 162 | CH₃CH₂O- | 3 | CH₃ | Cl | mp 60-61° C. | 56.66 | 5.76 | 9.44 | 7.30-6.78(m, 3H), 4.62-4.10 |

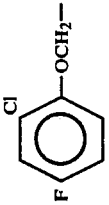

TABLE 1-continued

| Compound No. | R | n | X | Y | Physical properties | Element analysis (%) Calculated value (Measured value) | | | NMR (δ, ppm) |
|---|---|---|---|---|---|---|---|---|---|
| | | | | | | C | H | N | |
| | | | | | | (56.41) | (5.81) | (9.47) | (m, 4H), 3.25(t, 2H), 2.83–2.41 (m, 5H), 1.71(t, 3H) |
| 163 | CH₃CH₂OC(=O)— | 3 | CH₃ | Cl | mp 52–54° C. | 55.47 (55.58) | 5.29 (5.32) | 8.62 (8.58) | 7.00–6.40(m, 3H), 4.43(q, 2H), 3.98(t, 2H), 3.23(t, 2H), 2.60–2.20 (m, 2H), 2.20(s, 3H), 1.45(t, 3H) |
| 164 | CH₃NHC(=O)— | 3 | CH₃ | Cl | mp 98–99° C. | 54.28 (54.41) | 5.22 (5.18) | 13.56 (13.62) | 7.55(bs, 1H), 7.00–6.40(m, 3H), 3.98(t, 2H), 3.23(t, 2H), 2.78 (d, 3H), 2.40(m, 2H), 2.10(s, 3H) |
| 165 | (CH₃)₂NC(=O)— | 3 | CH₃ | Cl | oil | 55.64 (55.49) | 5.61 (5.59) | 12.97 (13.01) | 7.00–6.40(m, 3H), 7.98(t, 2H), 3.23(t, 2H), 2.90(s, 6H), 2.60–2.20(m, 2H), 2.10(s, 3H) |
| 166 | (CH₃CH₂)₂NC(=O)— | 3 | CH₃ | Cl | oil | 58.03 (57.88) | 6.32 (6.29) | 11.94 (11.97) | 7.00–6.40(m, 3H), 4.15–3.80 (m, 6H), 3.23(t, 2H), 2.60–2.20 (m, 2H), 2.20(s, 3H), 1.20(t, 6H) |
| 167 | CH₃CH₂CH₂— | 3 | Cl | Cl | oil | 53.35 (53.48) | 5.12 (5.09) | 8.89 (8.83) | 7.11–6.62(m, 3H), 3.95(t, 2H), 2.97(t, 2H), 2.70–2.10(m, 4H), 1.90–1.50(m, 2H), 0.98(t, 3H) |
| 168 | ClCH₂— | 3 | Cl | Cl | oil | 44.85 (44.72) | 3.42 (3.49) | 8.71 (8.73) | 7.31–6.65(m, 3H), 4.73(s, 2H), 4.01(t, 2H), 3.12(t, 2H), 2.67–2.10(m, 2H) |
| 169 | CH₃COCH₂— | 3 | Cl | Cl | oil | 48.71 (48.87) | 4.06 (4.03) | 8.12 (8.16) | 7.31–6.65(m, 3H), 5.12(s, 2H), 4.08(t, 2H), 3.15(t, 2H), 2.51–2.12(m, 5H) |
| 170 | HOCH₂— | 3 | Cl | Cl | mp 74–75° | 47.54 (47.32) | 3.96 (3.94) | 9.24 (9.28) | 7.31–6.65(m, 3H), 4.73(s, 2H), 4.55(bs, 2H), 4.01(t, 2H), 3.12 (t, 2H), 2.67–2.10(m, 2H) |
| 171 | 4-F, 2-Cl-C₆H₃OCH₂— | 3 | Cl | Cl | oil | 50.07 (50.21) | 3.25 (3.22) | 6.49 (6.45) | 7.31–6.62(m, 6H), 5.23(s, 2H), 4.02(t, 2H), 3.17(t, 2H), 2.42–2.12(m, 2H) |
| 172 | CH₃CH₂OC(=O)— | 3 | Cl | Cl | mp 57–58° C. | 48.71 (48.55) | 4.09 (4.05) | 8.11 (8.16) | 7.00–6.40(m, 3H), 4.43 (q, 2H), 3.98(t, 2H), 3.23(t, 2H), 2.60–2.20(m, 2H), 1.45(t, 3H) |

TABLE 1-continued

[Structure: R-C(=N-O-(CH₂)ₙ-O-Ar(X)(Y))]

| Compound No. | R | n | X | Y | Physical properties | Element analysis (%) Calculated value (Measured value) | | | NMR (δ, ppm) |
|---|---|---|---|---|---|---|---|---|---|
| | | | | | | C | H | N | |
| 173 | CH₃NHC(=O)— | 3 | Cl | Cl | mp 90-92° C. | 47.29 (47.48) | 3.98 (3.92) | 12.72 (12.61) | 7.55(bs, 1H), 7.00-6.40(m, 3H), 3.98(t, 2H), 3.23(t, 2H), 2.78(d, 3H), 2.60-2.20(m, 2H), 2.10(s, 3H) |
| 174 | (CH₃)₂NC(=O)— | 3 | Cl | Cl | mp 60-61° C. | 48.85 (48.99) | 4.40 (4.38) | 12.20 (12.09) | 7.00-6.40(m, 3H), 3.98(t, 2H), 3.23(t, 2H), 2.90(s, 6H), 2.60-2.20(m, 2H) |

The compounds of the present invention may be used as they are but normally they are used in the form such as wettable powders, dusts, emulsion concentrates, suspension concentrates, or granules. These formulations may be used as they are or may be used after dilution with water.

When liquid formulations are applied, the solvent such as water, alcohol, ether, acetone, ester, amide or petroleum ether may be used. As the solid carrier, an inorganic powder such as magnesium lime, gypsum, calcium carbonate, silica, alumina, zeolite, clay mineral and resin powder may be used.

The dosage of the present invention to be used as an active ingredient may be varied depending on the type of formulation, the manner for application, the timing and the weather condition. The dosage is usually varied in the range of 0.25 to 4 Kg/ha.

The compounds of the present invention are sufficiently effective even if they are applied solely. However, their application in combination with one or more types of compounds having herbicidal activity makes it possible not only to reduce the amount of the active ingredient, but also to attain the enlargement of the herbicidal spectrum or improve the effects.

The typical examples of herbicides that can be used together with the compounds of the present invention are mentioned, for examples, amide-type herbicides such as monalide, propanil, solan, diphenamide, fluoridamide, mefluidine, benzamizole, butachlor and alachlor; dinitroaniline-type herbicides such as trifluralin, benfluralin, profluralin, isopropaline, pendimenthalin and ethalfluralin; urea-type herbicides such as buturon, monolinuron, parafluron, tetrafluron, linuron, sulfodiazol, buthiuron, chlorosulfuron and sulfomethuron-methyl; carbamate-type herbicides such as chlorobufam, barban, diallate, phenmedipham, butylate, triallate, bentiocarb and methylbencarb; diphenylether-type herbicides such as oxyfluorofen, acifluorfornethyl, lactofen, formesafen and fluoronitrofen; and diazine-type herbicides such as oxadiazon and immazaqium.

FORMULATION EXAMPLES

Some examples of the formulations are given below.

Formulation 1

Emulsion Concentrate 30 parts of compound No. 1 of the present invention, 60 parts of m-xylene and 10 parts of surfactant mixture(-polyoxyethylene alkyl aryl ether and sodium alkyl aryl sulfate) were uniformly mixed and stirred to obtain an emulsion concentrate.

Formulation 2

Wettable Powder 10 parts of compound No. 4 of the present invention, 85 parts of white carbon and 5 parts of surfactant mixture(polyoxyethylene alkyl aryl ether sulfate and polyoxyethylene alkyl and aryl ether) were mixed and pulverized to obtain a wettable powder.

Formulation 3

Granule 3 parts of compound No. 100 of the present invention, 60.0 parts of bentonite, 35 parts of talc, 0.5 parts of sodium dodecyl benzene sulfonate, 0.5 parts of sodium metasilicate and 1.5 parts of sodium tripolyphosphate were mixed, and after an addition of a proper amount of water, kneaded. The mixture was granulated by using an extrusion granulating machine and dried by a conventional method to obtain granules.

TEST EXAMPLE

Test Example 1

Herbicidal Test Against Paddy Field Weeds

Paddy field soil was filled in 140 cm$^2$ plastic pot and irrigated. Paddy rice seedlings (Variety: Dongjin) of 2.5 leaf stage were transplanted and some amounts of paddy field weeds were also sown. On the second day after the transplantation, the predetermined amounts of the compounds of the present invention were applied in the form of wettable powder.

During the test period, 2 cm in height of water from the surface of the soil in pot was maintained. Upon twentieth day after the treatment with compound of the present invention, the herbicidal effects against the weeds and phytotoxicity against paddy rice plants were examined. The results are shown in table 2 and herbicide rating system is shown in table 3.

TABLE 2

| Compound NO. | ORYSA | ECHOR | SCPJU | BR.s | ANEKE | MOOVA | CYPDI | CYPSE | SAGPY |
|---|---|---|---|---|---|---|---|---|---|
| | | | | | | | | | 4 kg/ha |
| 1 | 70 | 95 | | | 100 | 100 | 100 | | |
| 2 | 40 | 100 | | | 100 | 100 | 100 | | |
| 3 | 10 | 50 | 0 | | 70 | | 10 | | |
| 4 | 30 | 100 | 100 | | 100 | 100 | 100 | | |
| 5 | 30 | 90 | 100 | | 100 | 100 | 100 | | |
| 6 | 40 | 100 | 100 | 100 | | | | 100 | 20 |
| 7 | 20 | 100 | 90 | | 100 | 100 | 100 | | |
| 8 | 0 | 100 | 50 | | 100 | 100 | 70 | | |
| 9 | 20 | 100 | 100 | | 100 | 100 | 100 | | |
| 10 | 30 | 100 | 100 | | 100 | 100 | 100 | | |
| 11 | 30 | 100 | 100 | | 100 | 100 | 100 | | |
| 12 | 20 | 100 | 100 | | 100 | 100 | 100 | | |
| 13 | 0 | 100 | 100 | | 100 | 100 | 100 | | |
| 14 | 0 | 80 | 70 | | 100 | 100 | 80 | | |
| 15 | 30 | 100 | 90 | | 100 | 90 | 100 | | |
| 16 | 0 | 90 | 100 | | 100 | 90 | 100 | | |
| 17 | 30 | 100 | 100 | | 100 | 100 | 100 | | |
| 18 | 50 | 100 | 100 | | 100 | 100 | 100 | | |
| 19 | 80 | 100 | 100 | 100 | | | | | 100 |
| 20 | 20 | 100 | 100 | | 100 | 100 | 100 | | |

TABLE 2-continued

| Compound NO. | ORYSA | ECHOR | SCPJU | BR.s | ANEKE | MOOVA | CYPDI | CYPSE | SAGPY 4 kg/ha |
|---|---|---|---|---|---|---|---|---|---|
| 21 | 10 | 100 | 100 | 100 | | | | 100 | 100 |
| 22 | 60 | 100 | 100 | 100 | | | | 100 | 100 |
| 23 | 10 | 100 | 100 | 100 | | | | 100 | 100 |
| 24 | 10 | 100 | 100 | 100 | | | | 100 | 100 |
| 25 | 10 | 100 | 100 | 100 | | | | 100 | 100 |
| 26 | 10 | 100 | 100 | 100 | | | | 100 | 100 |
| 27 | 10 | 100 | 100 | 100 | | | | 100 | 100 |
| 28 | 0 | 100 | 100 | 100 | | | | 100 | 20 |
| 29 | 20 | 100 | 100 | 100 | | | | 70 | 100 |
| 30 | 80 | 100 | 100 | 100 | | | | 100 | 100 |
| 31 | 40 | 100 | 100 | 100 | | | | 100 | 100 |
| 32 | 30 | 100 | 90 | | | | 100 | 100 | 70 |
| 33 | 30 | 100 | 100 | 100 | | | | | 100 |
| 34 | 50 | 100 | 100 | 100 | | | | | 100 |
| 35 | 60 | 100 | 100 | 100 | | | | 100 | 100 |
| 36 | 60 | 100 | 100 | 100 | | | | 100 | 100 |
| 37 | 60 | 100 | 100 | 100 | | | | 100 | 50 |
| 38 | 10 | 100 | 100 | 100 | | | | 100 | 100 |
| 39 | 10 | 100 | 100 | 100 | | | | 100 | 100 |
| 40 | 70 | 100 | 100 | | 100 | 100 | 100 | | |
| 41 | 70 | 100 | 100 | | 100 | 100 | 100 | | |
| 42 | 50 | 80 | 100 | | 100 | 100 | 100 | | |
| 43 | 50 | 100 | 100 | 100 | | | | | 100 |
| 44 | 50 | 100 | 100 | 100 | | | | | 100 |
| 45 | 10 | 100 | 100 | 100 | | | | 100 | 70 |
| 46 | 0 | 40 | 70 | 50 | | | | | |
| 47 | 20 | 100 | 100 | 100 | | | | 100 | 100 |
| 48 | 10 | 100 | 100 | 100 | | | | 100 | 100 |
| 49 | 10 | 100 | 100 | | 100 | 100 | 50 | | |
| 50 | 40 | 100 | 90 | 100 | | | | | 50 |
| 51 | 20 | 100 | 80 | 100 | | | | | 20 |
| 52 | 40 | 100 | 100 | 100 | | | | 100 | 90 |
| 53 | 70 | 100 | 100 | | 100 | 100 | 100 | | |
| 54 | 40 | 80 | 100 | | 100 | 100 | 100 | | |
| 55 | 0 | 50 | 20 | | 100 | 90 | 60 | | |
| 56 | 20 | 90 | 90 | | 100 | 100 | 80 | | |
| 57 | 0 | 100 | 90 | | 100 | 100 | 100 | | |
| 58 | 40 | 70 | 20 | | 80 | 70 | 50 | | |
| 59 | 30 | 70 | 70 | | 80 | 80 | 80 | | |
| 60 | 20 | 80 | 100 | | 100 | 100 | 100 | | |
| 61 | 40 | 80 | 90 | | 100 | 100 | 100 | | |
| 62 | 10 | 90 | 90 | | 100 | 100 | 100 | | |
| 63 | 20 | 90 | 100 | | 100 | 100 | 100 | | |
| 64 | 60 | 100 | 100 | | 100 | 100 | 100 | | |
| 65 | 50 | 100 | 100 | | 100 | 100 | 100 | | |
| 66 | 40 | 100 | 100 | | 100 | 100 | 100 | | |
| 67 | 10 | 100 | 100 | | 100 | 100 | 100 | | |
| 68 | 20 | 100 | 90 | 100 | | | | | 0 |
| 69 | 40 | 100 | 100 | 100 | | | | 100 | 100 |
| 70 | 30 | 100 | 90 | 100 | | | | 100 | 80 |
| 71 | 50 | 100 | 100 | 100 | | | | 100 | 100 |
| 72 | 10 | 100 | 100 | 100 | | | | 100 | 100 |
| 73 | 10 | 100 | 100 | 100 | | | | 100 | 100 |
| 74 | 60 | 100 | 100 | 100 | | | | 100 | 100 |
| 75 | 100 | 100 | | | 100 | 100 | 100 | | |
| 76 | 10 | 90 | 90 | | 100 | 90 | 100 | | |
| 77 | 60 | 100 | | | 100 | 100 | 100 | | |
| 78 | 80 | 100 | 100 | | 100 | 100 | 100 | | |
| 79 | 40 | 100 | | | 100 | 100 | 100 | | |
| 80 | 40 | 100 | 100 | 100 | | | | 100 | 80 |
| 81 | 40 | 100 | 100 | 100 | | | | 100 | 60 |
| 82 | 50 | 100 | 100 | 100 | | | | 100 | 100 |
| 83 | 10 | 60 | 50 | 60 | | | | 50 | 50 |
| 84 | 10 | 80 | 90 | 100 | | | | 60 | 90 |
| 85 | 50 | 100 | 90 | 100 | | | | 100 | 100 |
| 86 | 60 | 100 | 100 | 100 | | | | 100 | 100 |
| 87 | 40 | 100 | 100 | 100 | | | | 90 | 100 |
| 88 | 0 | 50 | 0 | 30 | | | | 0 | 0 |
| 89 | 70 | 100 | 100 | 100 | | | | 100 | 100 |
| 90 | 60 | 100 | 100 | 100 | | | | 100 | 100 |
| 91 | 10 | 100 | 100 | 100 | | | | 100 | 100 |
| 92 | 10 | 100 | 100 | 100 | | | | 100 | 100 |
| 93 | 60 | 100 | 100 | 100 | | | | 100 | 100 |
| 94 | 30 | 100 | 100 | | 100 | 100 | 100 | | |
| 95 | 50 | 100 | 100 | 100 | | | | 100 | 90 |
| 96 | 40 | 100 | | | 100 | 100 | 70 | | |
| 97 | 60 | 100 | | | 100 | 100 | 100 | | |
| 98 | 60 | 100 | | | 100 | 100 | 100 | | |
| 99 | 20 | 100 | 100 | | 100 | 100 | 90 | | |

TABLE 2-continued

| Compound NO. | ORYSA | ECHOR | SCPJU | BR.s | ANEKE | MOOVA | CYPDI | CYPSE | SAGPY |
|---|---|---|---|---|---|---|---|---|---|
| | | | | | | | | | 4 kg/ha |
| 100 | 60 | 100 | 100 | | 100 | 100 | 100 | | |
| 101 | 80 | 100 | 100 | 100 | | | | 100 | 100 |
| 102 | 50 | 100 | 100 | | 100 | 100 | 100 | | |
| 103 | 60 | 100 | 100 | 100 | | | | 100 | 100 |
| 104 | 60 | 90 | | | 100 | 100 | 90 | | |
| 105 | 50 | 100 | 100 | | 100 | 100 | 100 | | |
| 106 | 0 | 100 | 80 | 80 | | | | | 0 |
| 107 | 20 | 100 | 100 | 80 | | | | | 30 |
| 108 | 10 | 100 | 70 | 100 | | | | | 0 |
| 109 | 60 | 100 | 100 | 100 | | | | 100 | 100 |
| 110 | 60 | 100 | 100 | 100 | | | | | 100 |
| 111 | 10 | 100 | 100 | 100 | | | | 100 | 100 |
| 112 | 50 | 100 | 100 | 100 | | | | 100 | 100 |
| 113 | 60 | 100 | 100 | 100 | | | | 100 | 100 |
| 114 | 10 | 100 | 100 | 100 | | | | 100 | 100 |
| 115 | 10 | 100 | 100 | 100 | | | | 100 | 100 |
| 116 | 10 | 100 | 100 | 100 | | | | 100 | 100 |
| 117 | 10 | 100 | 100 | 100 | | | | 100 | 100 |
| 118 | 10 | 100 | 100 | 100 | | | | 100 | 100 |
| 119 | 60 | 100 | 100 | 100 | | | | | 100 |
| 120 | 60 | 100 | 100 | 100 | | | | 100 | 100 |
| 121 | 10 | 100 | 100 | 100 | | | | 100 | 100 |
| 122 | 10 | 100 | 100 | 100 | | | | 100 | 100 |
| 123 | 30 | 100 | 100 | 100 | | | | 100 | 60 |
| 124 | 50 | 100 | 100 | 100 | | | | 100 | 70 |
| 125 | 70 | 100 | 60 | 100 | | | | 90 | 100 |
| 126 | 70 | 100 | 100 | 100 | | | | 100 | 100 |
| 127 | 60 | 100 | 100 | 100 | | | | 100 | 100 |
| 128 | 60 | 100 | 100 | 100 | | | | | 100 |
| 129 | 70 | 100 | 100 | 100 | | | | | 100 |
| 130 | 80 | 100 | 100 | 100 | | | | 100 | 100 |
| 131 | 60 | 100 | 100 | 100 | | | | | 100 |
| 132 | 50 | 100 | 100 | 100 | | | | 80 | 90 |
| 133 | 40 | 100 | 90 | 100 | | | | 100 | 80 |
| 134 | 50 | 100 | 100 | 100 | | | | 100 | 80 |
| 135 | 30 | 100 | 100 | 100 | | | | 100 | 100 |
| 136 | 10 | 100 | 100 | 100 | | | | 100 | 100 |
| 137 | 10 | 100 | 100 | 100 | | | | 100 | 100 |
| 138 | 10 | 100 | 100 | 100 | | | | 100 | 100 |
| 139 | 10 | 100 | 100 | 100 | | | | 100 | 100 |
| 140 | 40 | 90 | 80 | 100 | | | | 90 | 0 |
| 141 | 50 | 100 | 90 | 100 | | | | 100 | 0 |
| 142 | 50 | 100 | 80 | 100 | | | | 100 | 0 |
| 143 | 70 | 100 | 100 | 100 | | | | 100 | 80 |
| 144 | 70 | 100 | 100 | 100 | | | | 100 | 90 |
| 145 | 70 | 100 | 100 | 100 | | | | 100 | 100 |
| 146 | 60 | 100 | 100 | 100 | | | | 100 | 70 |
| 147 | 60 | 100 | 100 | 100 | | | | 100 | 90 |
| 148 | 10 | 100 | 100 | 100 | | | | 100 | 100 |
| 149 | 10 | 100 | 100 | 100 | | | | 100 | 100 |
| 150 | 80 | 100 | 100 | 100 | | | | 100 | 100 |
| 151 | 10 | 100 | 100 | 100 | | | | 100 | 100 |
| 152 | 10 | 100 | 100 | 100 | | | | 100 | 100 |
| 153 | 50 | 100 | 100 | 100 | | | | 100 | 100 |
| 154 | 90 | 100 | 100 | 100 | | | | 100 | 100 |
| 155 | 10 | 100 | 100 | 100 | | | | 100 | 100 |
| 156 | 10 | 100 | 100 | 100 | | | | 100 | 100 |
| 157 | 10 | 100 | 100 | 100 | | | | 100 | 100 |
| 158 | 20 | 100 | 100 | | 100 | 100 | 100 | | |
| 159 | 0 | 20 | 80 | 90 | | | | 90 | 20 |
| 160 | 30 | 70 | 100 | 100 | | | | 70 | |
| 161 | 40 | 100 | 100 | 100 | | | | 70 | 100 |
| 162 | 40 | 60 | 100 | 100 | | | | 100 | 70 |
| 163 | 60 | 80 | 100 | 100 | | | | 100 | 100 |
| 164 | 10 | 40 | 100 | 100 | | | | 50 | 90 |
| 165 | 0 | 60 | 100 | 100 | | | | 90 | 100 |
| 166 | 0 | 40 | 90 | 100 | | | | 80 | 90 |
| 167 | 30 | 100 | 100 | | 100 | 100 | 100 | | |
| 168 | 10 | 60 | 50 | 60 | | | | 50 | 50 |
| 169 | 20 | 100 | 100 | 100 | | | | 50 | 90 |
| 170 | 0 | 100 | 90 | 100 | | | | 0 | 60 |
| 171 | 10 | 80 | 40 | 100 | | | | 0 | 0 |
| 172 | 20 | 90 | 100 | 60 | | | | '50 | 50 |
| 173 | 0 | 50 | 90 | 100 | | | | 0 | 0 |
| 174 | 0 | 80 | 90 | 100 | | | | 0 | 70 |

*BR.s: mixture of annual broad leaf weeds such as ANEKE (dayflower), MOOVA (monochoria), ROTIN (toothcup) etc.

| PADDY WEED SPECIES | | |
|---|---|---|
| ABRV. | GENUS-SPECIES NAME | ENGLISH NAME |
| ORYSA | *Oryza sativa* L. | Rice |
| ECHOR | *Echinochloa crus-galli* P. BEAUV. var. *oryzicola* OHWI | Barnyardgrass |
| SCPJU | *Scirpus juncoides* ROXB. | Bulrush |
| CYPDI | *Cyperus difformis* L. | Umbrellaplant |
| CYPSE | *Cyperus serotinus* ROTTB. | Flat-sedge |
| ANEKE | *Aneilema keisak* HASSK. | Dayflower |
| MOOVA | *Monochoria vaginalis* PRESL. | Monochoria |
| ROTIN | *Rotala indica* KOEHE. | Toothcup |
| SAGPY | *Sagittaria pygmaea* MIQ. | Arrow head |

TABLE 3

| Herbicide Rating System | | | |
|---|---|---|---|
| Rating Percent Control | Description of Main categories | Crop Description | Weed Description |
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | effect | Crop injury more lasting, recovery | Deficient to moderate weed control |
| 60 | | Lasting crop injury no recovery | Moderate weed control |
| 70 | Severe effect | Heavy injury and stand loss | Control somewhat less than satisfactory |
| 80 | | Crop nearly destroyed a few survivors | Satisfactory to good weed control |
| 90 | | Only occasional live plants left | Very good to excellent control |
| 100 | Complete effect | Complete crop destruction | Complete weed destruction |

We claim:

1. A 1,2,4-oxadiazole derivative of the formula

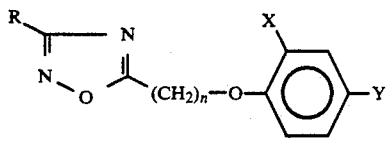

wherein

X represents a chlorine or fluorine atom or methyl group,

Y represents a chlorine or fluorine atom, n is 1 or 3, and

R represents a phenoxy group unsubstituted or substituted by chlorine atom, fluorine atom or $C_2$ alkoxy group; an amino group unsubstituted or substituted by $C_5$ alkyl, acetyl, $C_{1-2}$ alkoxycarbonyl, methylcarbamyl group or phenylsulfonyl group; a bromine atom or chlorine atom; a carbonyl group substituted by $C_{1-4}$ alkylamino, $C_{1-2}$ dialkylamino, $C_{1-2}$ alkoxy, amino, azido, halophenylamino, acetylamino, methylsulfonylamino, $C_{1-4}$ alkyl, benzyl or phenyl group; an oxime group substituted by $C_{1-4}$ alkyl or phenyl group; or an imine group substituted by $C_{1-2}$ alkoxy, amino, hydroxyamino group, ethylphosphonyl group or chlorine atom.

2. A herbicidal composition comprising as an active ingredient one or more compounds of formula (I) as defined in claim 1 and an inorganic carrier.

3. A 1,2,4-oxadiazole derivative of the formula (I) according to claim 1, wherein X represents a chlorine atom, Y represents a chlorine atom, n is 1, and R represents a carbonyl group substituted by $C_{1-4}$ alkylamino, $C_{1-2}$ dialkylamino, $C_{1-2}$ alkoxy, amino, azido, halophenylamino, acetylamino, methylsulfonylamino, $C_{1-4}$ alkyl, benzyl or phenyl group; an oxime group substituted by $C_{1-4}$ alkyl or phenyl group.

4. A compound having the structural formula of 3-(dimethylamino) carbonyl-5-(2',4'-dichlorophenoxy)methyl-1,2,4-oxadiazole.

* * * * *